United States Patent [19]

Fujiwhara et al.

[11] 4,148,656
[45] Apr. 10, 1979

[54] LIGHT-SENSITIVE SILVER HALIDE COLOR PHOTOGRAPHIC MATERIALS

[75] Inventors: Mitsuto Fujiwhara, Hachioji; Takashi Sasaki, Hino; Takashi Uchida, Hachioji; Morio Kobayashi, Sagamihara, all of Japan

[73] Assignee: Konishiroku Photo Industry Co., Ltd., Tokyo, Japan

[21] Appl. No.: 860,738

[22] Filed: Dec. 14, 1977

[30] Foreign Application Priority Data

Dec. 17, 1976 [JP] Japan .................... 51-152752

[51] Int. Cl.$^2$ .............................. G03C 1/40
[52] U.S. Cl. ..................... 96/100 R; 96/55; 96/56; 96/56.4; 96/56.5
[58] Field of Search ............ 96/55, 56.5, 56, 100, 96/56.4

[56] References Cited

U.S. PATENT DOCUMENTS

| | | | |
|---|---|---|---|
| 3,519,429 | 7/1970 | Lestina | 96/56 |
| 3,764,337 | 10/1973 | Arai et al. | 96/76 |
| 3,930,866 | 1/1976 | Oishi et al. | 96/56.5 |

Primary Examiner—J. Travis Brown
Attorney, Agent, or Firm—Haseltine, Lake & Waters

[57] ABSTRACT

A color photosensitive material comprising a support and a silver halide photosensitive layer containing compounds as represented by the following formula:

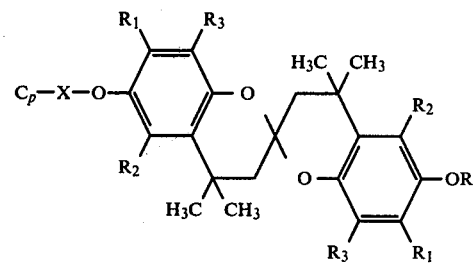

wherein R, $R_1$, $R_2$, $R_3$, $C_p$, and X are as herein defined, is described.

15 Claims, No Drawings

LIGHT-SENSITIVE SILVER HALIDE COLOR PHOTOGRAPHIC MATERIALS

This invention relates to light-sensitive silver halide color photographic materials, particularly light-sensitive silver halide color photographic materials containing novel couplers capable of forming dye images improved in light fastness.

Formation of color photographic images according to a subtractive process is generally carried out by subjecting a light-sensitive silver halide color photographic material (hereinafter called "color photosensitive material") to color development by the use of an aromatic primary amine type developing agent in the presence of a cyan coupler, a magenta coupler and a yellow coupler. In that case, the silver halide particles present in the exposed color photosensitive material are reduced by the developing agent and the oxidation product of said developing agent simultaneously formed thereby reacts by coupling with the couplers to form a cyan dye, magenta dye and yellow dye respectively, thereby forming a photographic color image.

Each coupler may be incorporated into a color photosensitive material. Generally color photosensitive materials of the type, into which the couplers are incorporated, are called the color photosensitive material of an internal type, and color photosensitive materials which are processed after exposure with a color developing solution into which the couplers are incorporated are called the color photosensitive materials of an external type.

The present invention is concerned with the internal type color photosensitive materials having incorporated therein the couplers.

As yellow couplers to form yellow dyes, there are used generally compounds having open chain active methylene groups. Magenta couplers used to form magenta dyes generally include compounds having closed chain active methylene groups such as a pyrazolone, pyrazolinobenzimidazole, indazolone or pyrazolotriazole nucleus, and each of such compounds forms an azomethine dye on color development. On the other hand, cyan couplers used to form cyan dyes include generally phenol type or α-naphthol type compounds and these compounds form indoaniline type dyes on color development.

Dye images obtained from such couplers on color development are desired that they do not subject to discoloring or fading even when stored at high temperature and high humidity.

However, such dye images as referred to above are not found yet to be satisfactory in their fastness to an ultraviolet ray or a visible ray. It is well known that such dye images are easily discoloring or fading when irradiated with these actinic rays. Further, unreacted couplers which remain mainly in unexposed areas of developed color photosensitive materials undergo chemical change to form the so-called yellow stain (hereinafter called "Y-stain"). Such discoloring or fading as mentioned above comes into question in the case of color image prints which are irradiated with actinic rays for a long period of time.

In order to overcome such drawbacks, various proposals have heretofore been made.

For instance, a process in which various ultraviolet absorbers are incorporated into color photographic materials (refer to U.S. Pat. Nos. 3,159,646, 3,004,896, 3,253,921 and 3,214,436, British Pat. No. 991,204, 991,603 and 1,026,142 and French Pat. No. 1,585,596), a process in which fading inhibitors having phenilic hydroxyl groups are incorporated into color photographic materials (refer to Japanese Patent Publication Nos. 31256/1973, 31625/1973 and 20977/1974, U.S. Pat. Nos. 3,069,262 and 2,360,290, and Japanese Laid-Open-to-Public Publication Nos. 27333/1976, 3432300/1976, 3574627/1976, 3573050/1976 and 27333/1976).

However, there is a limit to such processes for the improvement as relying on these additives. For instance, for satisfying light fastness, relatively large amounts of such additives are required to be incorporated into color photographic materials, thereby to bring about often such disadvantages as coloration and increase in film thickness due to the use of large amounts of additives, degradation of sharpness associated with the use thereof and so on. In addition to the improvement relying on the additives used, it is also known to improve light fastness by the use of couplers of various structures, said structures being suitably selected for the purpose.

For instance, there are proposed couplers having o-hydroxyphenylbenztriazole nucleus which is an ultraviolet absorbing group; pyrazolone type magenta couplers and phenol type cyan couplers having phenolic hydroxyl groups as stabilizing groups in U.S. Pat. Nos. 3,519,429 and 3,880,661; and couplers having hydroquinone diether groups as groups capable of giving light fast dyes. The couplers having ultraviolet absorbing groups, however, have no effect on prevention of fading due to visible ray, though they are effective on fading due to ultraviolet ray. The couplers having stabilizing groups, on the other hand, are not sufficiently stable when contacted with such high alkali solution as color developer and bring about a side reaction. Thus, these couplers are not satisfactory yet for fading prevention effects.

Further, the couplers are required to have such properties that not only the dyes thereby formed are excellent in stability but also the couplers, per se. are excellent in color developability, solubility in organic solvents and dispersion stability in silver halide emulson, sufficiently high in densities formed thereby, and the light absorption wavelength regions thereof are found in desirable ranges, and that various characteristics of silver halide emulsions into which the couplers are incorporated are excellent.

An object of the present invention is to provide couplers having a particularly strong light fastness, said couplers being capable of satisfying various characteristics required for photographic couplers.

A further object of the present invention is to provide color photosensitive materials containing couplers capable of giving dye images improved in stability to light.

As a results of extensive studies, the present inventors have found that the above-mentioned object of the present invention can be accomplished by incorporating at least one of the compounds (hereinafter called "the present couplers") represented by the following general formula [I] into a color photosensitive material.

General formula [I]

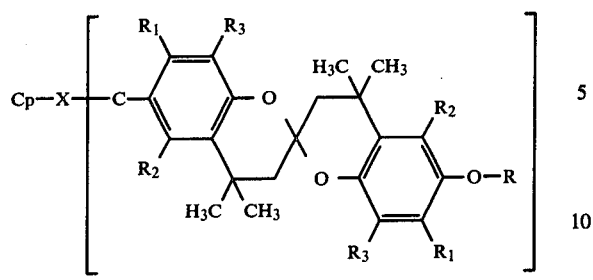

In the above-mentioned general formula [I], Cp represents such coupler residue bonded to the coupling or non-coupling position such as a yellow coupler residue (e.g. of open chain active methylene type yellow couplers), a magenta coupler residue (e.g. of 5-pyrazolone type couplers, pyrazolinobenzimidazole type couplers, indazolone type couplers, pyrazolonetriazole type couplers and cyanoacetyl type couplers) and a cyan coupler residue (e.g. phenol type couplers, α-naphthol type couplers and pyrazoloquinazolone type couplers), $R_1$, $R_2$ and $R_3$ individually represent hydrogen, halogen (e.g. fluorine, chlorine and bromine), an alkyl group (e.g. methyl, ethyl, n-propyl, i-propyl, n-butyl, i-butyl, sec-butyl, t-butyl, n-octyl and n-dodecyl), an alkenyl group (e.g., allyl and octenyl), an aryl group (e.g. phenyl and naphthyl), an alkoxy group (e.g. methoxy, ethoxy, butoxy and dodecyloxy), an alkenyloxy group (e.g. allyloxy), an aryloxy group (e.g. phenoxy), an alkylthio group (e.g. methylthio, ethylthio, butylthio and octylthio), an alkenylthio group (e.g. allylthio), an arylthio group (e.g. phenylthio), an acyl group (e.g. acetyl and benzoyl), an acylamino group (e.g. acetylamino and benzoylamino), a diacylamino group, an acyloxy group (e.g. acetyloxy and benzoyloxy), a sulfonamido group, an alkylamino group, a cycloalkyl group (e.g. cyclopentyl, cyclohexyl and cycloheptyl), or an alkoxycarbonyl group e.g. methoxycarbonyl, ethoxy carbonyl and butoxycarbonyl), R represents hydrogen, an alkyl group (e.g. methyl, ethyl, n-propyl, i-propyl, n-butyl, t-butyl, n-amyl, i-amyl, n-octyl, n-dodecyl and n-octadecyl, especially having 1–32 carbon atoms), an alkenyl group (e.g. allyl, octenyl and oleyl), a cycloalkyl group (e.g. cyclohexyl), an aryl group (e.g. phenyl and naphthyl), a heterocyclic ring (e.g. pyridinyl, pyradinyl, pyridadinyl, quinonyl, thienyl, piperidyl, pyrolyl, pyrrolinyl, tetrazolyl, thiadinyl, imidazolyl, morpholino, furyl, thiazolyl, oxazolyl, benzthiazolyl, benzoxazolyl, benzimidazolyl and furanyl), an acyl group (e.g. acetyl, propioloyl, octanoyl, dodecanoyl octadecanoyl, benzoyl and cinnamoyl), a carbamoyl group, a thiocarbamoyl group, a sulfamoyl group or Cp—X—, and X represents a simple bond, an alkylene group (e.g. methylene, ethylene, trimethylene, hexamethylene, octamethylene, dodecamethylene, propylene, ethylidene, butylidene and octylidene), a cycloalkylene group (e.g. cyclohexylene), an arylene group (e.g. phenylene), a divalent group in which at least one alkylene group and at least one arylene group have been connected (e.g., xylilene), a divalent heterocyclic group or a divalent group such as —CO—, —CS—, —SO$_2$—, —CONH— or —SO$_2$NH—, and $R_1$, $R_2$ and $R_3$ may be the same or different. The compounds of the aforesaid general formula [I], in which R is an alkyl group of 1 to 32 carbon atoms, $R_1$ is a lower alkyl group, $R_2$ and $R_3$ are individually hydrogen and X is a straight chain or a branched alkylene group having 1 to 22 carbon atoms are preferable, particularly said compounds in which $R_1$ is a methyl group is more preferable.

Hereinafter, the following structural unit is defined in the present specification as A.

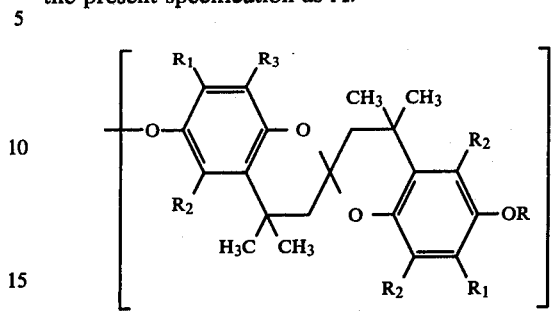

Of the couplers of the present invention, those which are particularly preferable may be the compounds represented by the following general formula [II].

General formula [II]

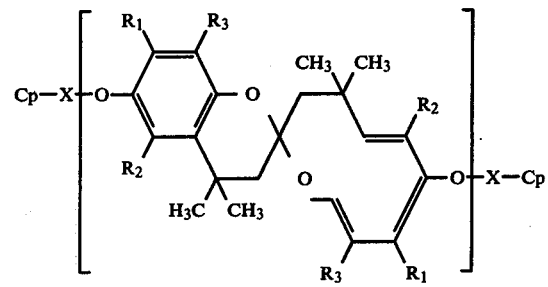

In the general formula [II] mentioned above, Cp, $R_1$, $R_2$, $R_3$ and X are the same as defined in the aforesaid general formula [I].

The compounds of the general formula [II] in which $R_1$, $R_2$ and $R_3$ are individually hydrogen or a lower alkyl group are preferable, and the compounds in which $R_1$ is a methyl group and $R_2$ and $R_3$ are individually hydrogen are more preferable.

In the aforementioned general formulas [I] and [II], Cp is a yellow, magenta or cyan coupler residue, as mentioned previously, preferably an acylacetonitrile yellow coupler residue, an acylacetanilide yellow coupler residue, an acylacetyl yellow coupler residue; a 5-pyrazolone magenta coupler residue, an imidazolone magenta coupler residue, a pyrazolinobenzimidazole magenta coupler residue (especially 5-pyrazolone coupler residue); a phenolcyan coupler residue, an α-naphthol cyan coupler residue and a pyrazoloquinazolone cyan coupler residue.

Useful yellow coupler residues are those represented by the following general formula [III].

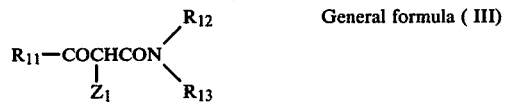

General formula (III)

wherein $R_{11}$, $R_{12}$ and $R_{13}$ individually represent a group used in ordinary 4-equivalent type acylacetanilide couplers, concretely $R_{11}$ typically includes, for example, an alkyl group (e.g. methyl, isobutyl, t-butyl, n-hexyl, t-hexyl, 1-methylpentyl, neopentyl, isohexyl, t-octyl and n-dodecyl), terpenyl group (e.g. norbonyl), an aryl group (e.g. phenyl and naphthyl) and a heterocyclic ring (e.g. furanyl, pyridyl, thiazolyl, oxazolyl, benzooxazolyl and imidazolyl).

$R_{12}$ and $R_{13}$ are individually a group which may be the same or different, for example, hydrogen, an alkyl group (e.g. methyl, ethyl, n-butyl or n-dodecyl) and an aryl group (e.g. phenyl or naphthyl), and said alkyl and the aryl in said aryl groups may individually have such the substituent as explained later.

$Z_1$ represents hydrogen or a group capable of releasing at the time of coupling of the coupler with an oxidation product of color developing agent (hereinafter called "split-off group").

The split-off group includes such groups known in the photographic industry as halogen, —OR', —OCOR', —SR', —OCONHR', —OSO$_2$NHR', —NHCOR', —NHSO$_2$R' (R' represents hydrogen, an alkyl group, an aryl group or a heterocyclic ring), —SO$_3$H, —SCN, an azo group, or a heterocyclic ring such as preferably 5-6 membered heterocyclic ring containing nitrogen, oxygen and/or sulfur (e.g. tetrazolyl, triazolyl, thiazolinyl, thiazolyl, triazinyl, imidazolinyl, benzimidazolinyl, benzthiazolyl, benzoxazolyl, oxazolyl, or succinimido etc.).

Typical examples of these split-off groups are disclosed, for example, in Japanese Laid-Open-to-Public Publication Nos. 10135/1975, 91323/1975, 120334/1975, 91323/1975, 120334/1975, 130441/1975, 25228/1975, 37647/1976, 52828/1976 and 117422/1976, U.S. Pat. Nos. 3,617,291 and 3,227,550 and British Pat. No. 1,331,179.

However, at least one of $R_{11}$, $R_{12}$, $R_{13}$ and $Z_1$ is a group represented by the aforesaid A or an alkyl group, an aryl group or a heterocyclic ring including therein a group represented by A attached through X.

Among the Cp— represented by general formula [III], those which are especially of usefulness in the present invention are Cp— represented by the following general formulas [III-a] or [III-b] as mentioned below:

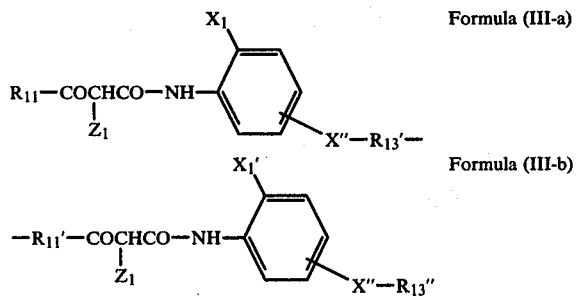

Formula (III-a)

Formula (III-b)

In general formula [III-a] and [III-b], $R_{11}$ and $Z_1$ are individually as defined in general formula [III].

$X_1'$ represents halogen, an alkoxy group or an aryloxy group, X" represents —NHCO—, —NHSO$_2$—, —COO—, —SO$_2$—, —NHCONH—, —CONH—, SO$_2$NH— or

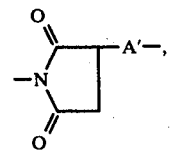

$R_{13}'$ represents an alkylene group, an arylene group, a cycloalkylene group or divalent heterocyclic ring, $R_{13}''$ represents an alkyl group, an aryl group, a cycloalkyl group or a heterocyclic ring, $R_{11}'$ represents an alkylene group or an arylene group, A' represents a simple bond, —O—, —S—, —SO$_2$— or

and $A_1'$ represents hydrogen, an alkyl group, an aryl group or an acyl group.

In the aforesaid general formula [III] and [III-a], $R_{11}$ is preferably a tert-alkyl group (e.g. tert-butyl, tert-amyl, tert-hexyl, tert-octyl and tert-dodecyl), an aryl group (e.g. phenyl), an alkaryl having an alkyl moiety of 1 to 15 carbon atoms (e.g. 4-methyl-phenyl, 2-methylphenyl, 3,5-dimethylphenyl, 4-butyl-phenyl, 4-octylphenyl and 4-dodecylphenyl) or an alkyl group, an aryl group or an alkaryl group including therein a group represented by A attached through X.

$R_{12}$ and $R_{13}$ are individually hydrogen or a phenyl substituted through X by halogen, an alkoxy group, a sulfonamido group, an acylamino group or a group represented by A, and $R_{12}$ and $R_{13}$ are not hydrogen simultaneously.

Useful magenta coupler residues are those which are represented by the following general formula [IV].

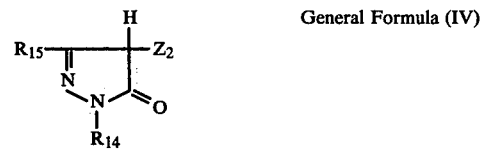

General Formula (IV)

wherein $R_{14}$ and $R_{15}$ individually represent a group used in ordinary 4-equivalent type pyrazolone type couplers, concretely $R_{14}$ represents hydrogen, an alkyl group (e.g. methyl, ethyl, isopropyl, t-butyl, n-hexyl, t-octyl, dodecyl and octadecyl especially having 1-32 carbon atoms), an alkenyl group (e.g. allyl), a cycloalkyl group (e.g. cyclohexyl), a terpenyl group (e.g. cyclohexyl), an aryl group (e.g. phenyl and naphthyl), a heterocyclic ring (e.g. pyridyl, quinolyl, furyl, thiazolyl, benzothiazolyl, oxazolyl, benzoxazolyl, imidazolyl, benzimidazolyl and naphthooxazolyl). Particularly useful group as $R_{14}$ is a phenyl group in which at least one of the ortho-positions of the phenyl has been substituted by an alkyl group, alkoxy group or halogen.

The $R_{15}$ substituent includes such group mentioned in the case of $R_{14}$ as an alkyl group, an aryl group or a heterocyclic ring.

$Z_2$ is the same as $Z_1$ defined in the aforementioned general formula [III], provided that at least one of $R_{14}$, $R_{15}$ and $Z_2$ is a group represented by A, a group represented by A through X, or an alkyl group, an aryl group or a heterocyclic ring including therein said group.

Among the Cp— represented by general formula [IV], those which are especially of usefulness in the present invention are Cp— represented by the following formula [IV-a] or [IV-b] as mentioned below:

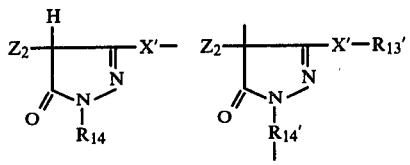

Formula (IV-a)   Formula (IV-b)

wherein $R_{14}$ represents an alkyl group, an aryl group or a heterocyclic ring, X' represents

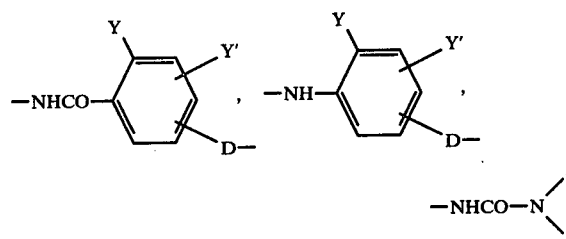

or —NHCO—, Y represents hydrogen, halogen, an alkyl group or an alkoxy group, Y' is Y, B represents hydrogen or an alkyl group, D represents —NHCO—, —CONH—, —NHSO₂—, —SO₂NH—,

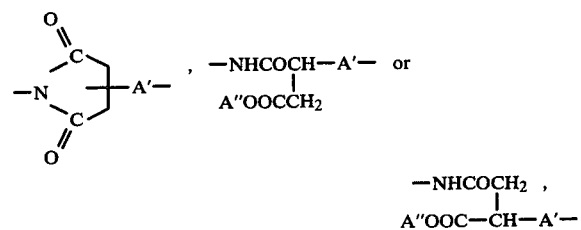

A' represents a simple bond, —O—, —S—, —SO₂— or $$-\underset{\underset{A_1'}{|}}{N}-$$

A" represents an alkyl group, $R_{14}'$ represents an alkylene group, an arylene group or a divalent heterocyclic ring, $Z_2$ represents hydrogen or a split-off group and $A_1$— represents hydrogen, an alkyl group, an aryl group or an acyl group.

In the aforesaid general formula [IV-a] and [IV-b], X' is preferably

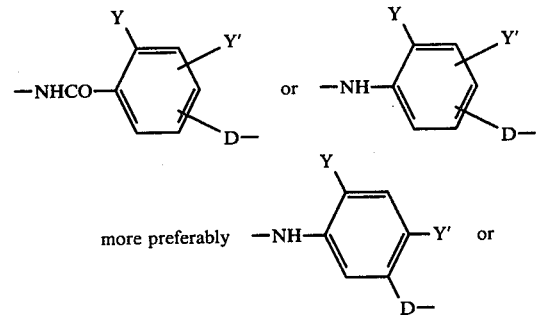

and $R_{14}'$ is preferably halogen-substituted phenylene, halogen-substituted alkylphenylene or halogen-substituted lower alkoxyphenylene.

In the aforesaid general formula [IV], $R_{14}$ is preferably halogen-substituted phenyl, halogen-substituted alkylphenyl, halogen-substituted lower alkoxyphenyl or the above-mentioned group represented by A substituted through X, and $R_{15}$ is an arylamino group or an acylamino group (the aryl of the aryl group may be substituted by a halogen atom, a lower alkyl group, a lower alkoxy group or a group represented by A substituted through X).

Useful cyan coupler residues are those which are represented by the following general formulas [V], [VI] and [VII].

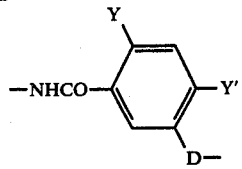

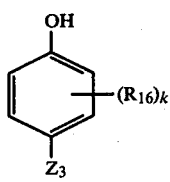

General formula (V)

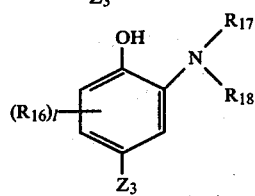

General formula (VI)

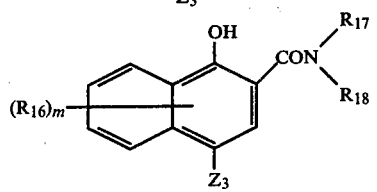

General formula (VII)

In the above-mentioned formulas, $R_{16}$, $R_{17}$ and $R_{18}$ individually represent a group used in ordinary 4-equivalent type phenol or α-naphthol couplers, concretely $R_{16}$ includes hydrogen, halogen, an aliphatic hydrocarbon group, an acylamino group, —O—$R_{19}$ or —S—$R_{19}$ (wherein $R_{19}$ is an aliphatic hydrocarbon group), and when two or more $R_{16}$ are present in the same one molecule, two or more $R_{16}$ may be different groups. $R_{17}$ and $R_{18}$ individually include an aliphatic hydrocarbon group, an aryl group or a heterocyclic ring, and one of $R_{17}$ and $R_{18}$ may be hydrogen. $R_{17}$ and $R_{18}$ may form together a nitrogen-containing heterocyclic ring, k is an integer of 1 to 4, l is an integer of 1 to 3, and m is an integer of 1 to 5. The aliphatic hydrocarbon group may be either saturated or unsaturated, or may be any of straight chain, branched and cyclized ones, and preferably this residue is an alkyl group (e.g. methyl, ethyl, propyl, isopropyl, butyl, t-butyl, isobutyl, dodecyl, octadecyl, cyclobutyl and cyclohexyl) and alkenyl group (e.g. allyl and octenyl). The aryl group includes a phenyl, naphthyl and the like groups. The heterocyclic ring includes typically a pyridinyl, pyradinyl, pyridadinyl, quinolyl, furaryl, thienyl, piperidyl, pyrrolyl, pyrrolinyl, tetrazolyl, thiadinyl, imidazolyl, morpholino, furyl, oxazolyl, thiazolyl, benzimidazolyl, benzoxazolyl and benzthiazolyl.

$Z_3$ is the same as $Z_1$ defined in the aforementioned general formula [III], provided that at least one of $R_{16}$, $R_{17}$, $R_{18}$ and $Z_3$ is a group represented by A through X, or an aliphatic hydrocarbon group, an acylamino group, an aryl group or a heterocyclic ring including therein said group represented by A attached through X.

Among the Cp— represented by general formulas [VI] and [VII], those which are especially of usefulness in the present invention are Cp— represented by the following formula [VI-a] or [VII-a] respectively as mentioned below:

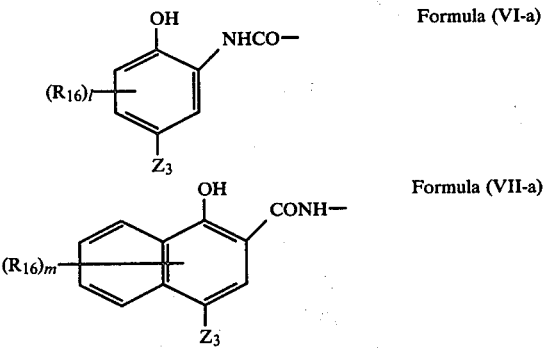

Formula (VI-a)

Formula (VII-a)

wherein $R_{16}$ represents hydrogen, halogen, an alkyl group or an acylamino group, $Z_3$ represents hydrogen or a split-off group, l represents 1-3 and m represents 1-5.

In the aforesaid general formula [VI-a], this which is especially of usefulness in the present invention is Cp— represented by the following formula [VI-a-1] as mentioned below:

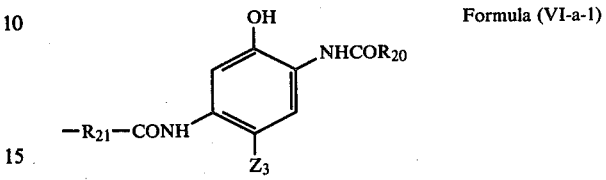

Formula (VI-a-1)

wherein $R_{20}$ represents an alkyl group, an aryl group, a heterocyclic ring or a cycloalkyl group and $R_{21}$ represents a simple bond, an alkylene group or an arylene group.

In the aforesaid general formula [IV-a], $R_{16}$ is preferably halogen or a methyl group.

Typical examples of the couplers of the present invention are exemplified below, but the compounds used in the invention are not limited to those exemplified.

Exemplified compound

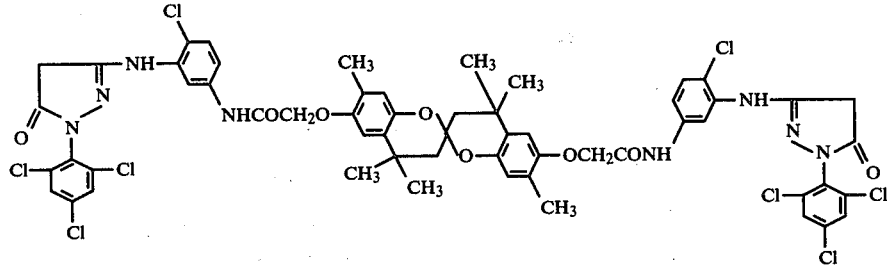

(M-1)

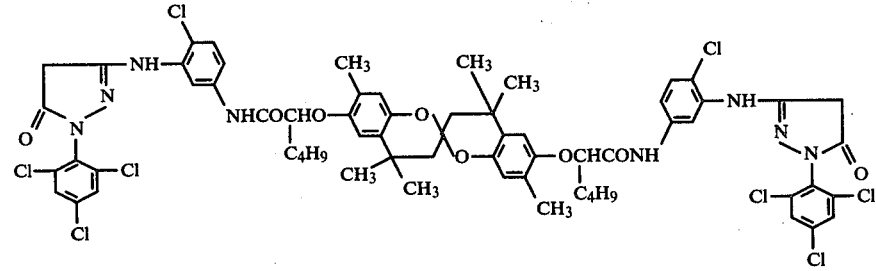

(M-2)

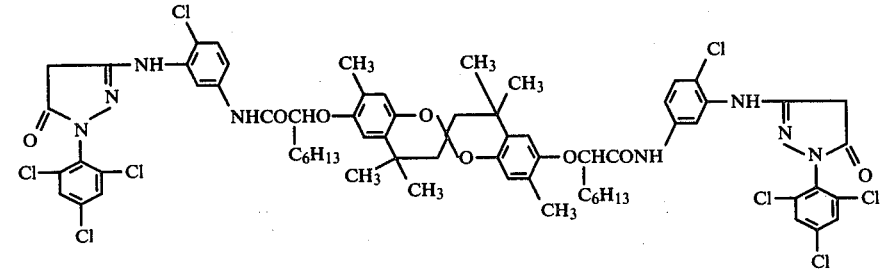

(M-3)

(M-4)
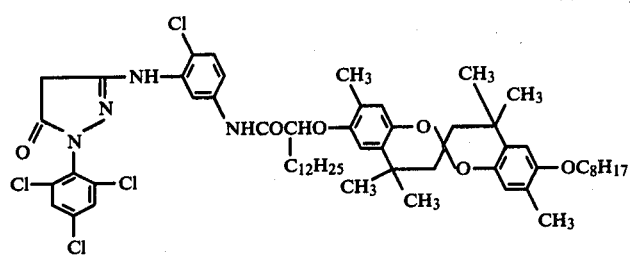
(M-5)
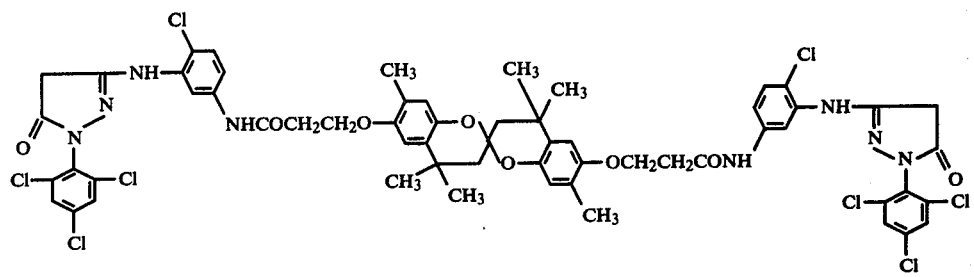
(M-6)
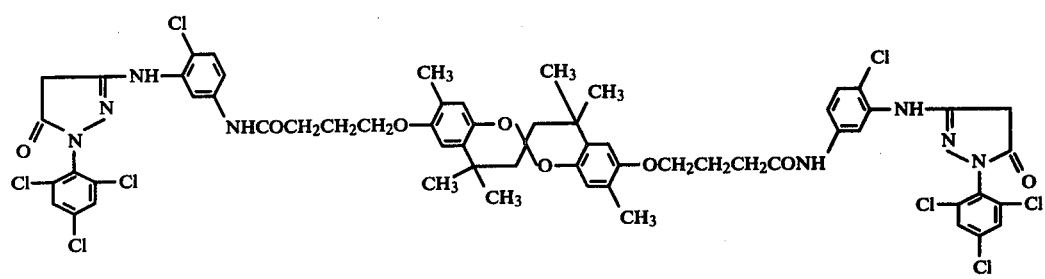
(M-7)
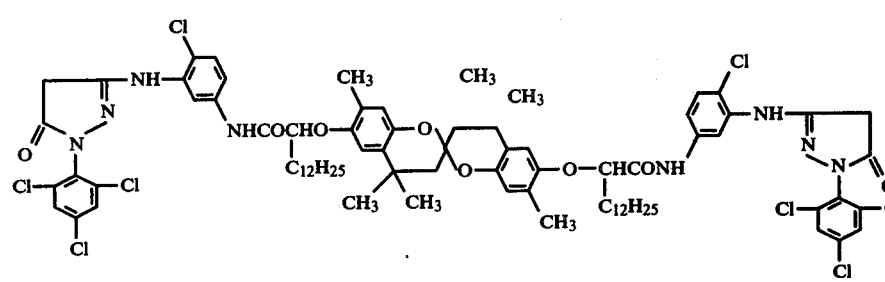
(M-8)
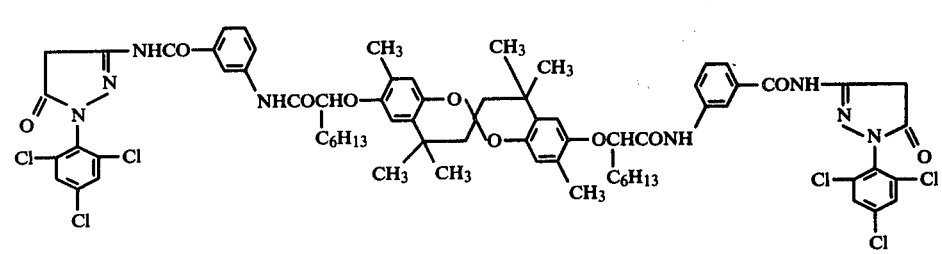
(M-9)
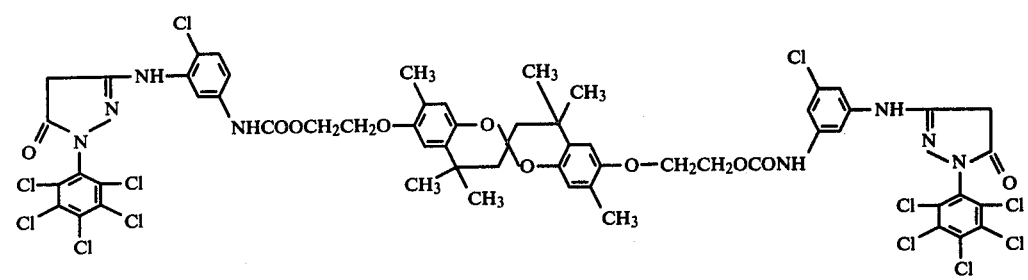

-continued
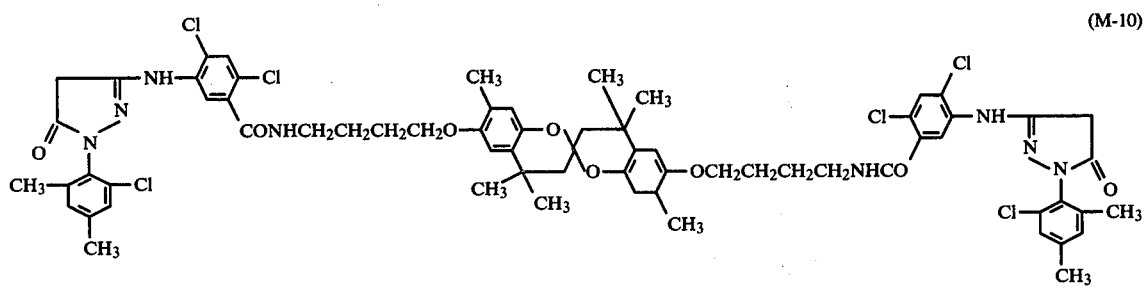
(M-10)
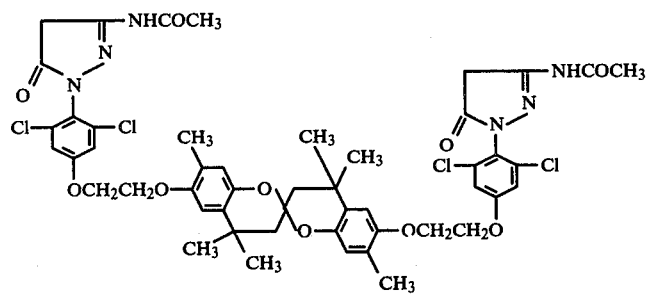
(M-11)
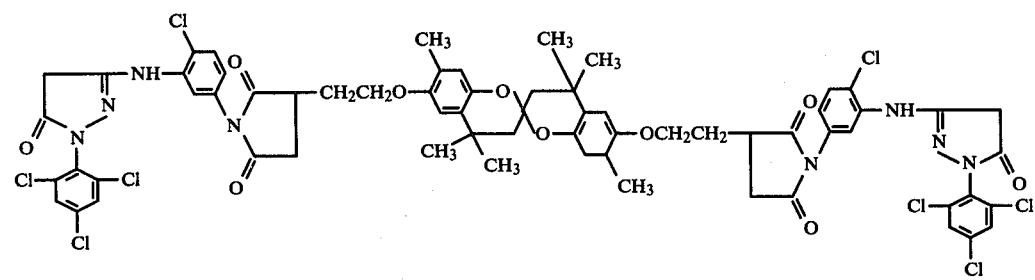
(M-12)
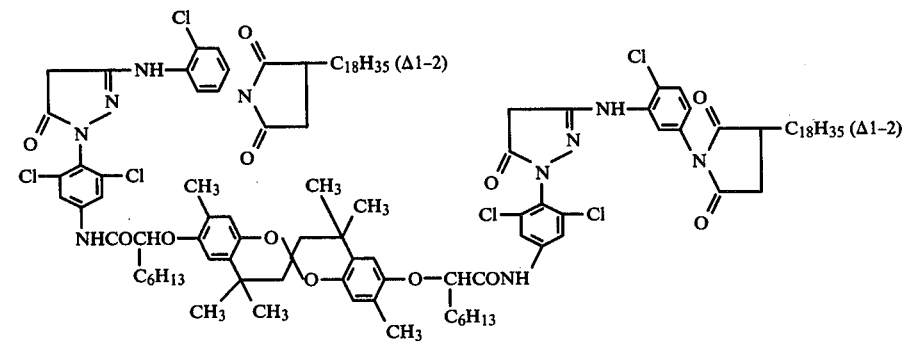
(M-13)
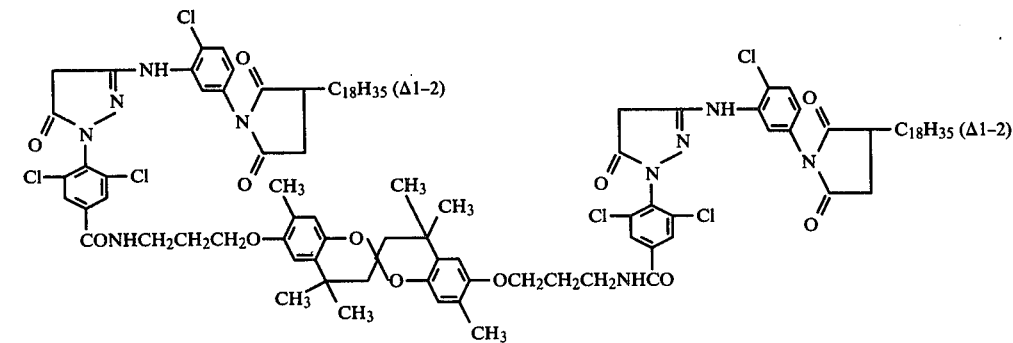
(M-14)

-continued
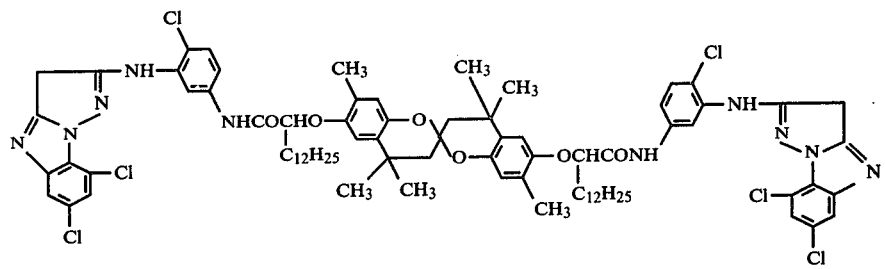
(M-15)
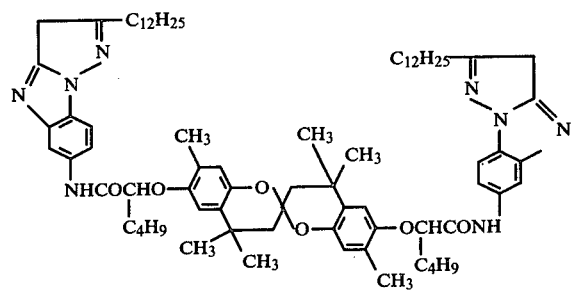
(M-16)
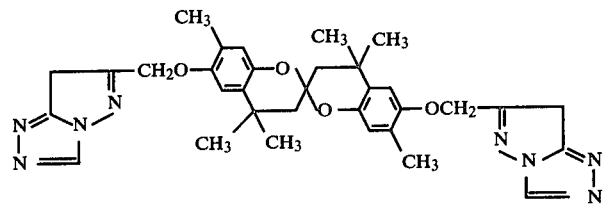
(M-17)
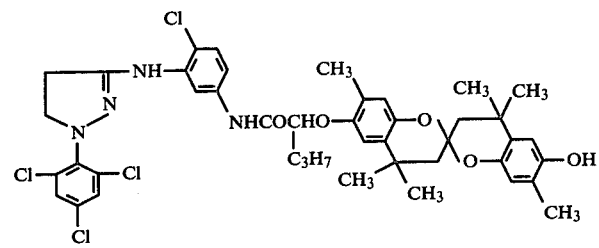
(M-18)
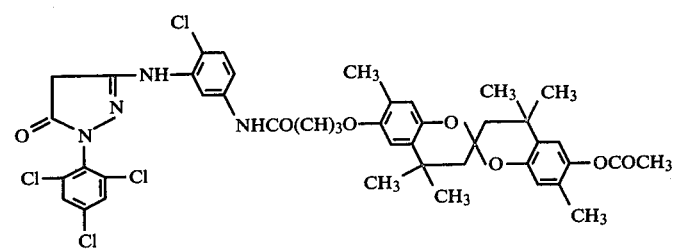
(M-19)
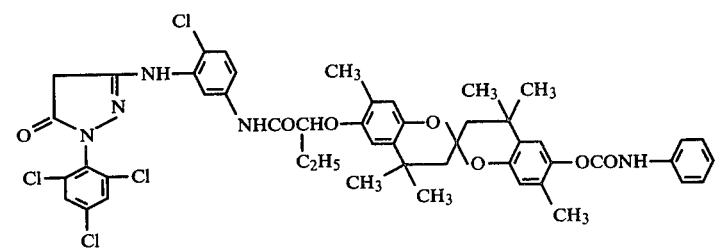
(M-20)

-continued
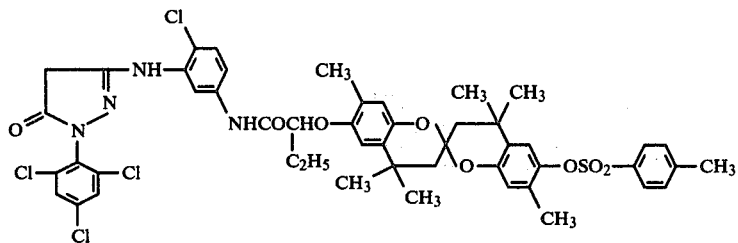
(M-21)
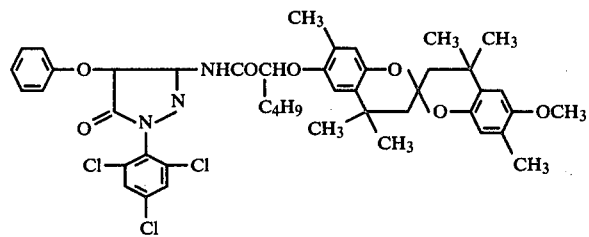
(M-22)
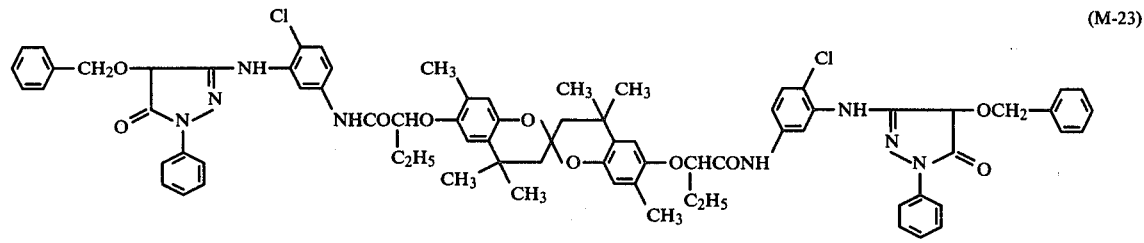
(M-23)
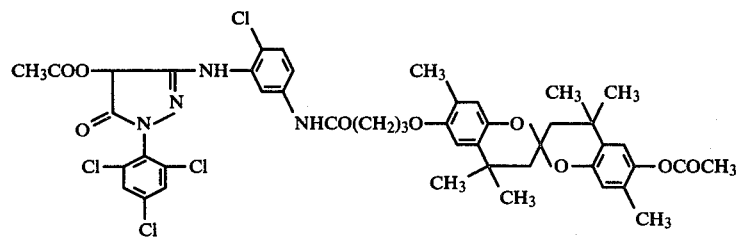
(M-24)
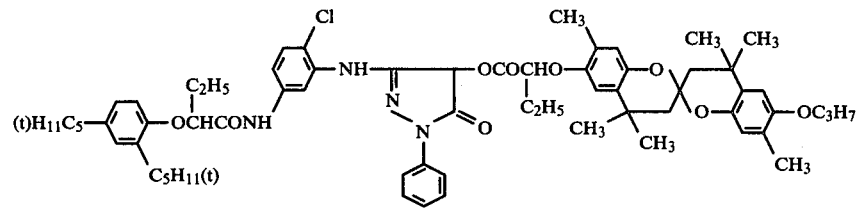
(M-25)
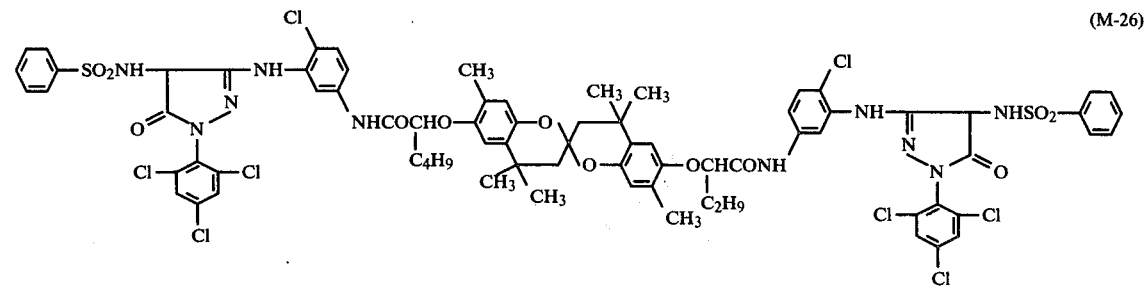
(M-26)

-continued
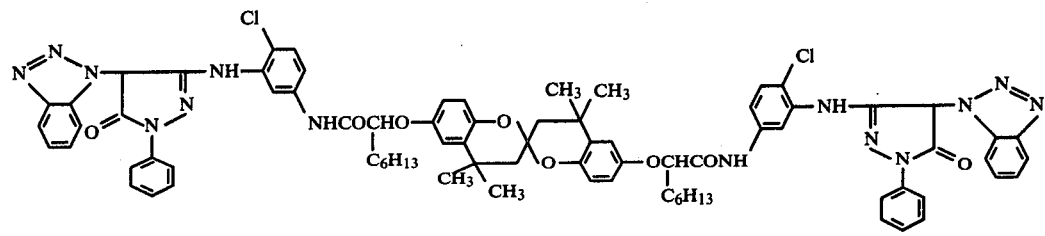
(M-27)
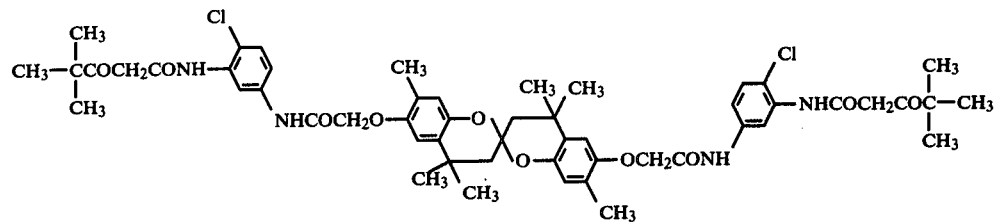
(Y-1)
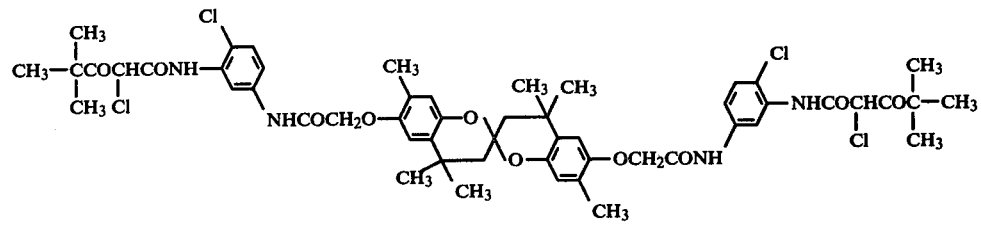
(Y-2)
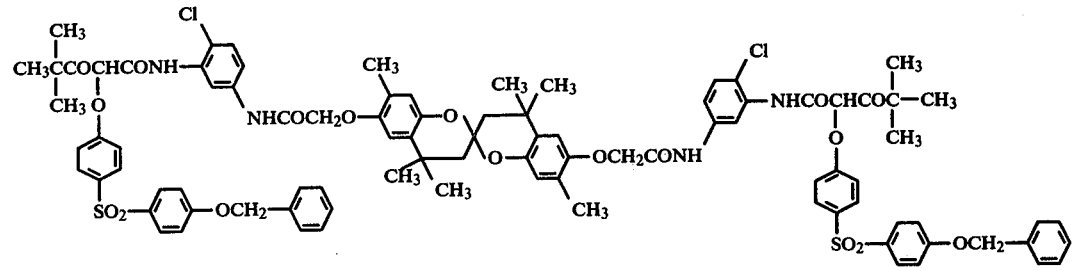
(Y-3)
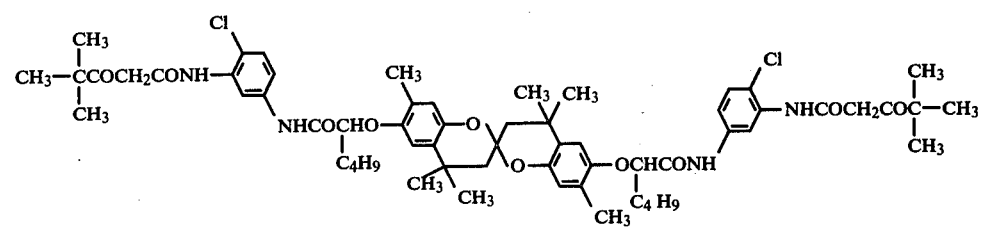
(Y-4)
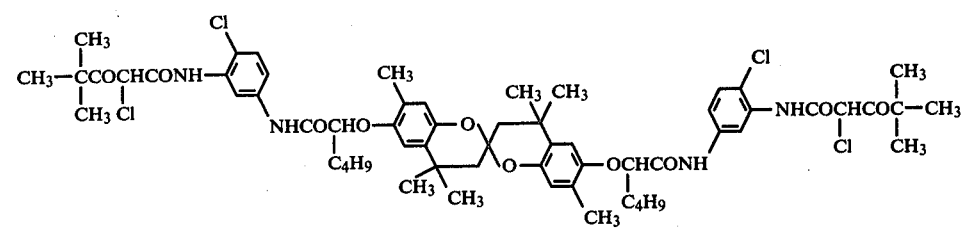
(Y-5)

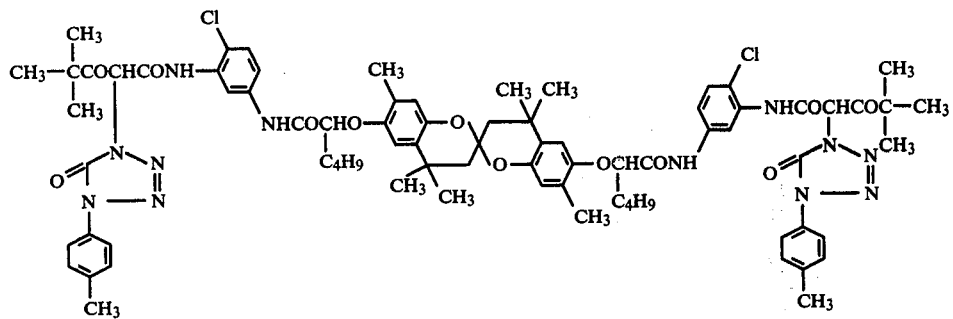
(Y-6)
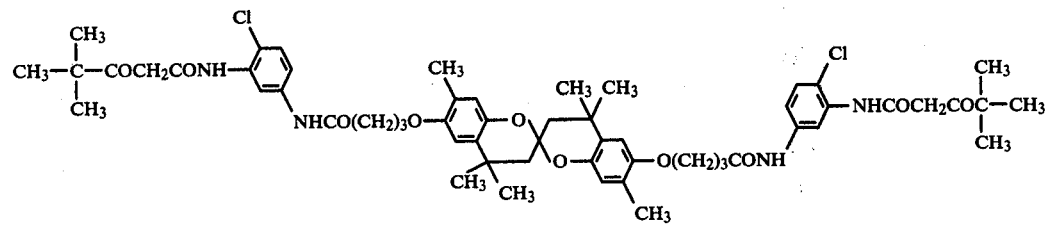
(Y-7)
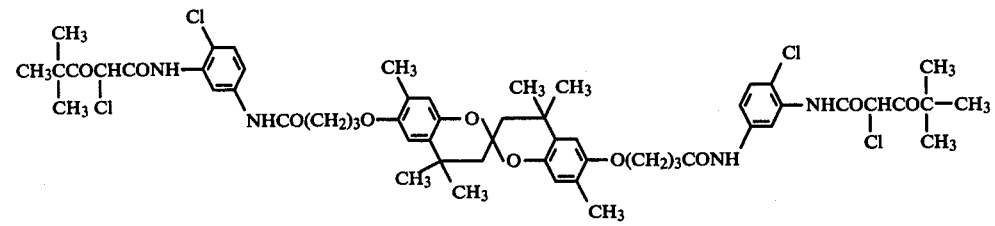
(Y-8)
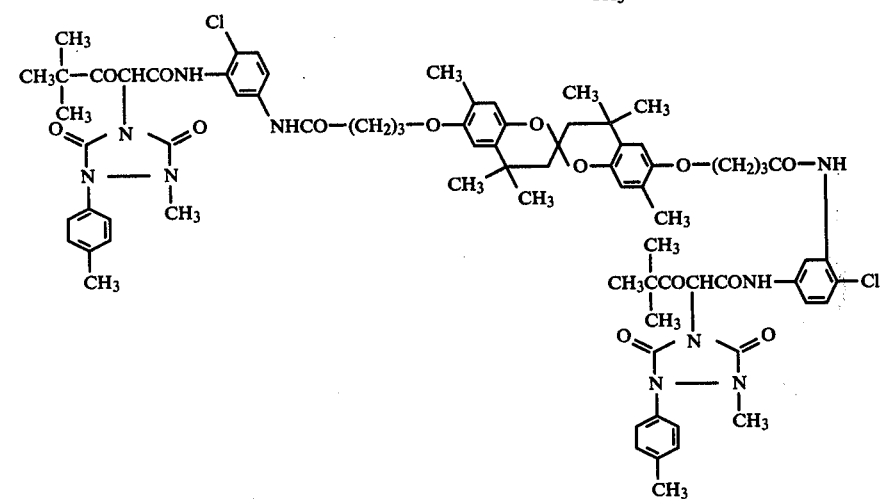
(Y-9)
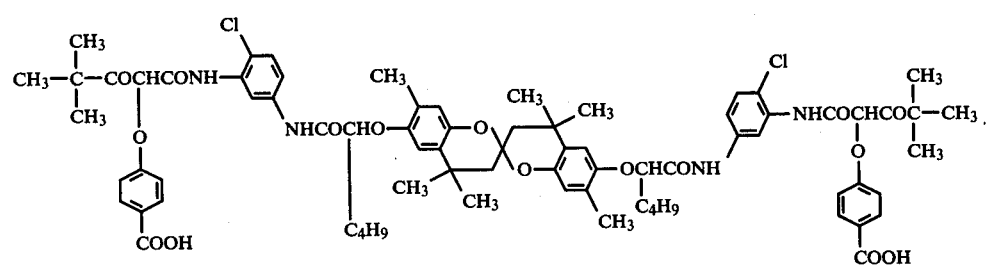
(Y-10)
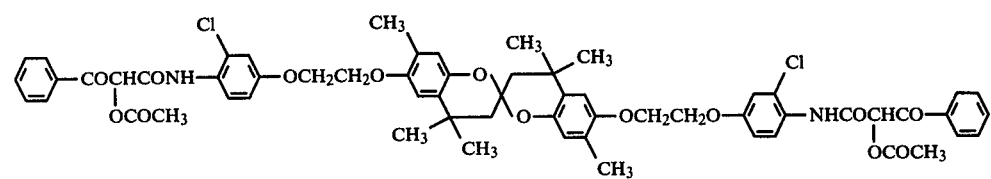
(Y-11)

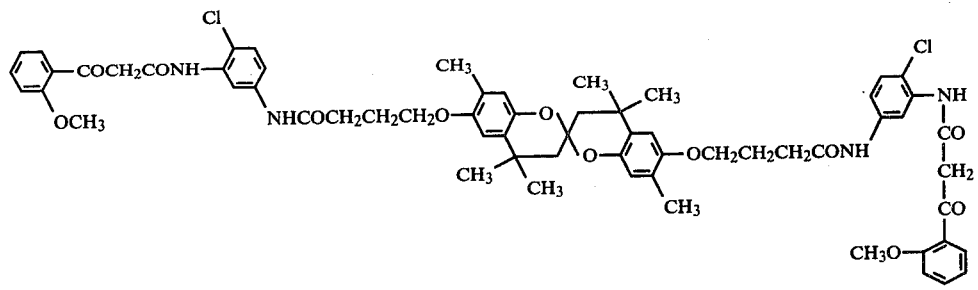
(Y-12)
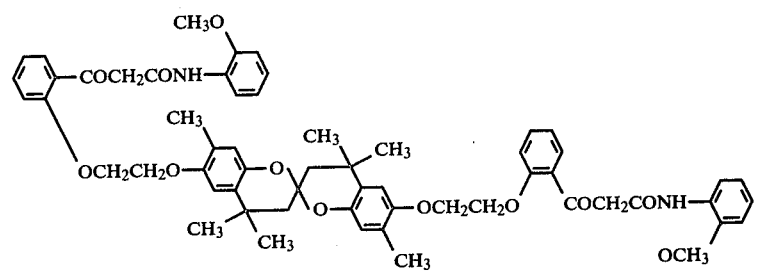
(Y-13)
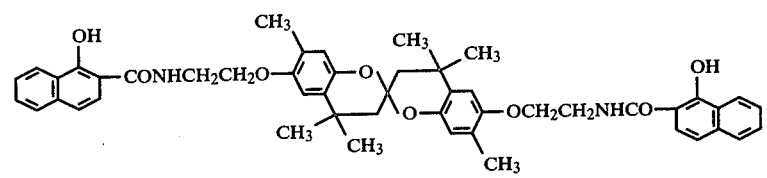
(C-1)
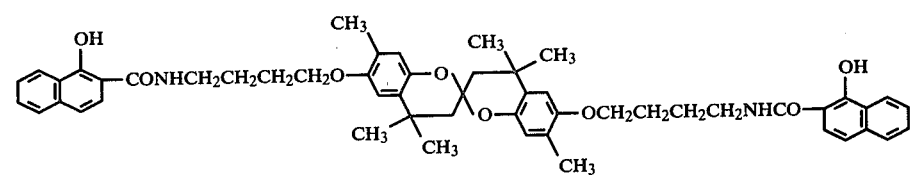
(C-2)
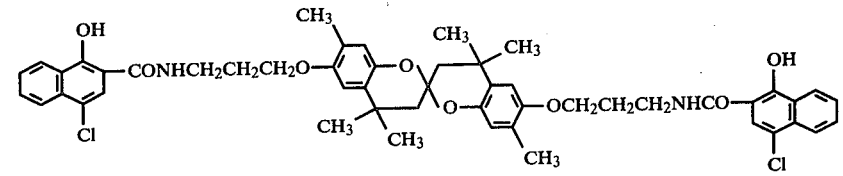
(C-3)
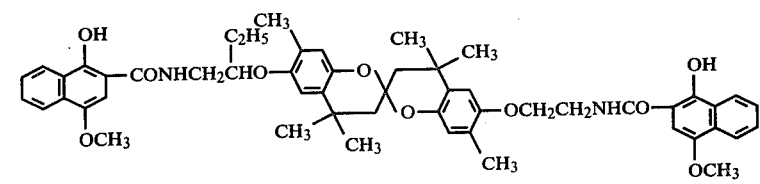
(C-4)
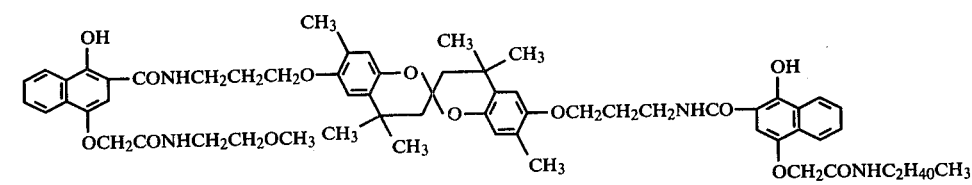
(C-5)

(C-6) 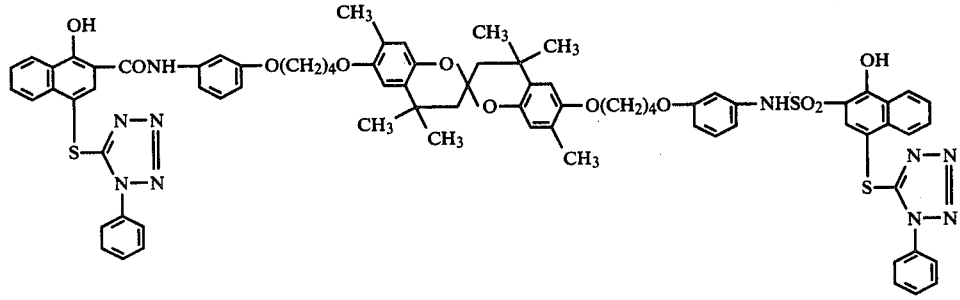
(C-7) 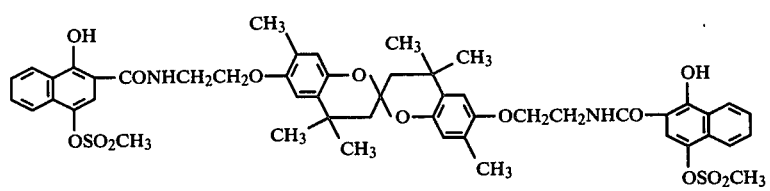
(C-8) 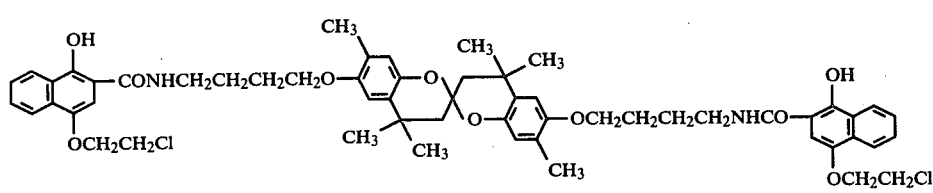
(C-9) 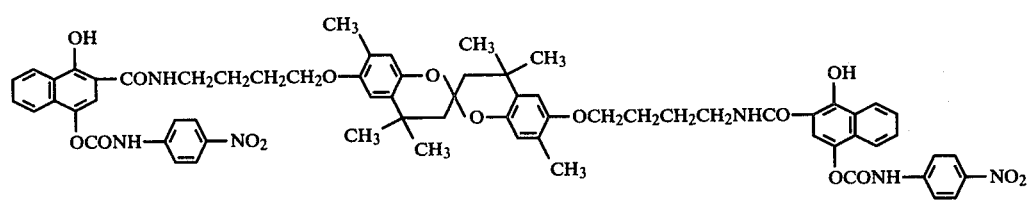
(C-10) 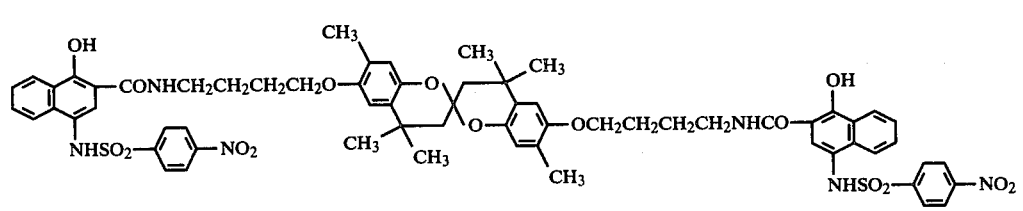
(C-11) 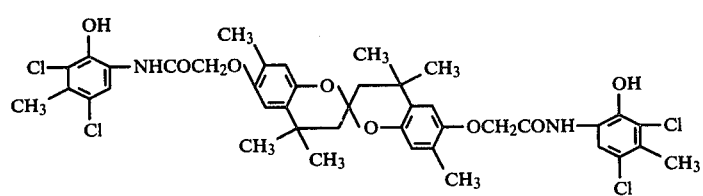
(C-12) 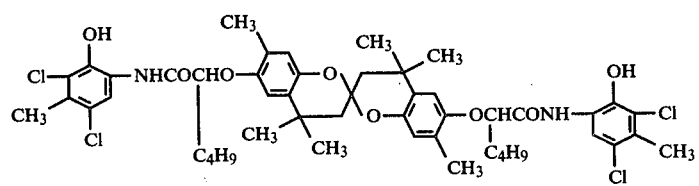
(C-13) 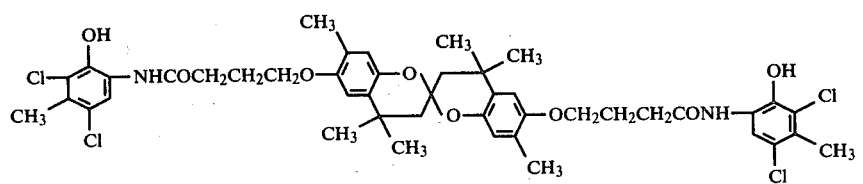

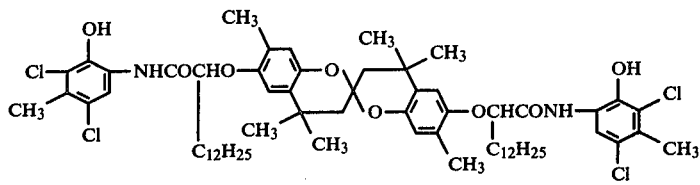

(C-14)

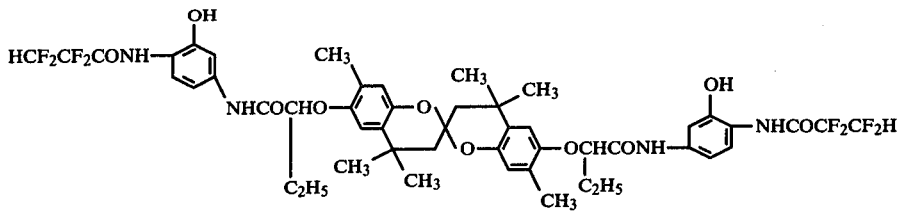

(C-15)

Synthesis examples of couplers of the present invention are set forth hereinafter.

SYNTHESIS EXAMPLE 1

Preparation of Exemplified compound (M-1)

a) Intermediate compound (1): Synthesis of (4,4,7,4',4',7'-hexamethyl-6,6'-diethoxycarbonylmethoxy-2,2'-spirobichroman)

In a solution of 95 g. of metallic sodium in 2 liters of absolute ethanol was dissolved 552 g. of 4,4,7,4',4',7'-hexamethyl-6,6'-dihydroxy-2,2'-spirobichroman, and the resulting solution was refluxed by heating for 30 minutes on a hot water bath. Thereafter, the ethanol was distilled off under reduced pressure, whereupon crystals were obtained. The crystals were suspended in 4 liters of xylene, and the resulting suspension was charged with 600 g. of ethyl α-bromoacetate, followed by refluxing by heating for 3 hours. The reaction liquid, after completion of reaction, was poured into 8 liters of water, thereby to separate the xylene layer therefrom. The water layer was extracted once with xylene, thereby to separate the xylene layer. Both xylene layers thus separated were combined together, and the combined xylene layer was washed with water and then dried on sodium sulfate. The crystals obtained by concentration of the solvent were recrystallized twice from 3.2 liters of methanol to obtain the desired product, m.p. 115°–118° C. The yield was 583 g. (in 72% yield).

b) Intermediate compound (2): Synthesis of (4,4,7,4',4',7'-hexamethyl-6,6'-bis-hydroxycarbonylmethoxy-2,2'-spirobichroman)

To a solution of 401 g. of the intermediate compound (1) in 6 liters of ethanol was added a solution of 185 g. of sodium hydroxide in 285 ml. of water and the resulting solution was allowed to undergo reaction under reflux for 1 hour on a hot water bath. After completion of reaction, about 1/2 of the ethanol was distilled off under reduced pressure, and the residue was poured into a solution comprising 5.8 liters of ice water mixture and 580 ml. of concentrated hydrochloric acid, whereby crystals were obtained. After water-washing, the crystals were thoroughly washed with ethanol to obtain a substantially pure desired product, m.p. 253°–254° C. The yield was 325 g. (in 91% yield).

c) Preparation of Exemplified compound (M-1)

A mixture comprising 135 g. of the intermediate compound (2), 130 g. of thionyl chloride and 3 cc of pyridine was allowed to undergo reaction with stirring under reflux, whereupon a yellow solution was gradually formed. After completion of a 1-hour reaction, the thionyl chloride was completely distilled off under reduced pressure, whereupon yellow crystals were obtained. The crystals were dissolved in 2 liters of acetonitrile, and the solution was added to a suspension of 203 g. of 1-(2,4,6-trichloro-phenyl)-3-(5-amino-2-chloroanilino)pyrazolone (5) in 200 ml. of acetonitrile. The resulting suspension was charged with 45 g. of pyridine and allowed to undergo reaction under reflux. After completion of a 2-hour reaction, the reaction liquid was cooled, and the deposited crystals were collected by filtration and then washed with water. After drying, the crystals were recrystallized three times from benzene to obtain a desired product, m.p. 202° C. The yield was 204 g. (in 58.23%). According to nuclear magnetic resonance spectrum (NMR), infrared absorption spectra (IR) and elementary analysis values as measured, it was confirmed that the product thus obtained was the end product.

Elementary analysis ($C_{57}H_{48}Cl_8N_8O_8$): Calculated (%) C:54.46; H:3.82; N:8.92; Cl:22.61; Found (%) C:54.17; H:3.98; N:9.15; Cl:22.32;

SYNTHESIS EXAMPLE 2

Preparation of Exemplified compound (M-3)

a) Intermediate compound (1): Synthesis of (4,4,7,4',4',7'-hexamethyl-6,6'-bis-(1-ethoxycarbonyl)-n-heptanoxy-2,2'-spirobichroman)

In a solution of 4.8 g. of metallic sodium in 250 ml. of absolute ethanol was dissolved 27.6 g. of 6,6'-dihydroxy-4,4,4',4',7,7'-hexamethyl-2,2'-spirobichroman, and the resulting solution was heated under reflux. After completion of reaction, the ethanol was distilled off, and the resulting crystals were suspended in 200 ml. of xylene. The resulting suspension was charged with 45 g. of ethyl α-bromooctanoate and heated under reflux. After completion of reaction, the reaction liquid was poured into 400 ml of water to obtain the xylene layer by separation. After water-washing, the xylene layer was washed with a cooled 10% aqueous sodium hydroxide solution, followed by water-washing, and then dried over sodium sulfate. After drying, the solvent was distilled off to obtain a syrup-like compound. The compound thus obtained was purified by silica gel chromatograph using benzene as a developing solvent to obtain a desired product in a syrup-like form. The yield was 34 g. (in 64.2% yield).

b) Intermediate compound (2): Synthesis of (4,4,7,4',4',7'-hexamethyl-6,6'-bis-(1-carboxy-n-heptoxy)-4,4,4',4',7,7'-hexamethyl-6,6'-bis-(1-hydroxycarbonyl)n-heptanoxy-2,2'-spirobichroman)

To a solution of 30 g. of the intermediate compound (1) in 300 ml. of ethanol was added a solution of 10.7 g. of sodium hydroxide in 16.5 ml. of water, and the resulting mixed solution was allowed to react under reflux. After one-hour reaction, one half of the ethanol was distilled off, and the residue was poured into a solution comprising 336 ml. of ice-cold water and 33.6 ml. of concentrated hydrochloric acid to deposit crystals. After washing followed by drying, the compound thus obtained was intended to be used in the subsequent reaction without subjecting to any particular purification.

c) Synthesis of Exemplified compound (M-3)

To a solution of 21.4 g. of the intermediate compound (2) in 150 ml. of carbon tetrachloride was added 7.6 g. of phosphorus pentachloride, and the resulting mixture was heated with thorough stirring for 1 hour under reflux on a hot water bath. After completion of reaction, the carbon tetrachloride and the resultant phosphorus oxychloride were completely distilled off. The resultant residue was dissolved in 300 ml. of anhydrous acetonitrile, and the solution was charged with 12.1 g. of 1-(2,4,6-trichloro-phenyl)-3-(5-amino-2-chloro)-5-pyrazolone. The resultant mixture was allowed to undergo reaction with stirring under reflux. After a 6-hour reaction, the mother liquor obtained by filtration was poured into 300 ml. of water and then extracted with ethyl acetate. After thorough water-washing, the extract was dried over sodium sulfate, and then the ethyl acetate was distilled off to obtain a compound in a syrup-like form. After thorough washing with n-hexane, the compound purified by means of silica gel chromatography using a 500:1 mixture of benzene and ethyl acetate as a developing solvent to obtain 23.4 g. of a compound in a syrup-like form in 50.1% yield. According to IR, NMR and elementary analysis values as measured, it was confirmed that the compound thus obtained was an end product.

Elementary analysis ($C_{60}H_{72}Cl_8N_8O_8$): Calculated (%) C:58.15; H:5.06; N:7.87; Cl:19.94 Found (%) C:57.99; H:5.05; N:8.01; Cl:19.81;

SYNTHESIS EXAMPLE 3

Preparation of Exemplified compound (M-7)

a) Intermediate compound (1): Synthesis of (6,6'-bis-(1-ethoxycarbonyl-n-tridecyloxy)-4,4,4,4',7,7'-hexamethyl-2,2'-spirobichroman)

In a solution of 5.5 g. of metallic sodium in 300 ml. of absolute ethanol was dissolved 36.8 g. of 4,4,7,4',4',7'-hexamethyl-6,6'-dihydroxy-2,2'-spirobichroman, and the resulting solution was heated for 30 minutes under reflux. After completion of reaction, crystals obtained by distilling off the ethanol were suspended in 300 ml. of xylene, and the suspension was charged with 74 g. of ethyl α-bromotetradecanoate and allowed to undergo reaction with stirring for 3.5 hours under reflux. After completion of reaction, the reaction liquid was poured into 300 ml. of water and then extracted with ligroin. The mixed layer of ligroin and xylene was washed with water and then washed with a cooled 10% aqueous sodium hydroxide solution, followed by water-washing, and then dried over sodium sulfate. After drying, the solvents were distilled off, and the residue was subjected to vacuum distillation to obtain a compound, b.p. 182°–186° C. The yield was 49.9 g. (in 56.9% yield).

b) Intermediate compound (2): Synthesis of (6,6'-bis-(1-carboxy-n-tridecyloxy)-4,4,4',4',7,7'-hexamethyl-2,2'-spirobichroman)

To a solution of 43.8 g. of the intermediate compound (2) in 300 ml. was added a solution of 16 g. of sodium hydroxide in 25 cc of water, and the resulting mixture was heated for 1 hour under reflux. After completion of reaction, the reaction liquid was poured into an aqueous solution comprising 500 ml of water and 50 ml. of concentrated hydrochloric acid to deposit crystals. The crystals separated by filtration were washed with water and then dried to obtain 38.2 g. (93.1% yield) of white crystals which were then used in the subsequent reaction without subjecting to any particular purification.

c) Synthesis of Exemplified compound (M-7)

A solution of 21.5 g. of the intermediate compound (2) in 150 ml. of carbon tetrachloride was charged with 5.2 g. of phosphorus pentachloride, and the resulting mixture was heated for 1 hour under reflux. After completion of reaction, the carbon tetrachloride and the resultant phosphorus oxychloride were completely distilled off. The residue thus obtained was dissolved in 300 ml. of anhydrous acetonitrile, and the solution was charged with 18.2 g. of 1-(2,4,6-trichloro-phenyl)-3-(5-amino-2-chloroanilino)-5-pyrazolone and heated with stirring under reflux. After a 6-hour reaction, the mother liquor separated by filtration was poured into 300 ml. of water and then extracted with ethyl acetate. After washing the extract with water followed by drying over sodium sulfate, the solvent was distilled off to obtain a syrup-like product. After washing with n-hexane, the syrup-like product was purified by means of silica gel chromatography using a 95:5 mixture of benzene and acetone to obtain 20.2 g. (51.3% yield) of the desired product in a syrup-like form. According to NMR, IR and elementary analysis, it was confirmed that the desired product was the title end product.

Elementary analysis ($C_{81}H_{96}Cl_8N_8O_8$): Calculated (%) C:61.06; H:6.03; N:7.04; Cl:17.84; Found (%) C:60.85; H:6.04; N:7.11; Cl:17.66;

SYNTHESIS EXAMPLE 4

Preparation of Exemplified compound (Y-4)

a) Intermediate compound (1): Synthesis of (6,6'-bis-(1-ethoxycarbonyl-n-pentyloxy-4,4,4',4',7,7'-hexamethyl-2,2'-spirobichroman)

To a solution of 5.5 g. (0.24 mole) of metallic sodium in 200 ml of absolute ethanol was added 37.6 g. (0.102 mole) of 6,6'-dihydroxy-4,4,4',4',7,7'-hexamethyl-2,2'-spirobichroman, and the resulting mixture was allowed to undergo reaction by heating under reflux. After completion of reaction, the ethanol was distilled off under reduced pressure, and the resultant crystals were suspended in 100 ml. of xylene. The suspension was charged with 44 g. (0.2 mole) of ethyl α-bromo-n-hexanoate and allowed to undergo reaction for 3 hours, by heating under reflux. After completion of reaction, the reaction liquid was poured into 1 liter of water, and the xylene layer formed was separated. The water layer was once extracted with xylene and both xylene layers thus obtained were combined together. After water-washing, the combined xylene layer was dried over sodium sulfate. The solvent was concentrated under reduced pressure, and the resulting viscous liquid was purified by means of silica gel chromatography using a 98:2 mixture of benzene and acetone as a developing solvent to obtain 46 g. (69% yield) of a pale yellow viscous liquid.

b) Intermediate compound (2): Synthesis of (6,6'-bis-(1-carboxy-n-pentoxy)-4,4,4',4',7,7'-hexamethyl-2,2'-spirobichroman)

To a solution of 33 g. (0.05 mole) of the intermediate compound (2) in 100 ml. of ethanol was added an aqueous solution of 20 ml. of 12 g. (0.3 mole) of sodium hydroxide, and the resulting mixture was hydrolyzed for 1 hour by heating under reflux. After completion of hydrolysis, about one half of the amount of the ethanol was distilled off under reduced pressure, and the residue was poured into 400 ml. of ice-cold water containing 38 ml. of concentrated hydrochloric acid, extracted with ethyl acetate, washed with water, dried over sodium sulfate and then concentrated under reduced pressure to obtain a pale yellow solid. The solid was recrystallized from a mixture of n-hexane and benzene to obtain 22 g. (74% yield) of white crystals, m.p. 153°–156° C.

c) Intermediate compound (3): Synthesis of (6,6'-bis-[1-(4-chloro-3-carbamoyl)n-pentoxy]-4,4,4',4',7,7'-hexamethyl-2,2'-spirobichroman)

To a solution of 18 g. (0.03 mole) of the intermediate compound (2) in 150 ml. of carbon tetrachloride was added 13.8 g. (0.066 mole) of phosphorus pentachloride, and the mixture was allowed to undergo reaction for 1 hour by heating under reflux. After evolution of hydrochloric acid was over, the resultant phosphorus oxychloride and the solvent were distilled off under reduced pressure to obtain a compound in a syrup-like form. A solution of this compound in 60 ml. of acetone was added dropwise to a solution comprising 10.4 g. (0.06 mole) of 4-chloro-3-nitroaniline, 5.7 g. of pyridine and 90 ml. of acetone, and the resulting mixture was then allowed to undergo reaction for 1 hour by heating under reflux. After completion of reaction, the reaction liquid was concentrated under reduced pressure, and the residue was dissolved in benzene. The benzene solution was washed several times with an aqueous hydrochloric acid solution and water and then dried over sodium sulfate. Concentration under reduced pressure gave yellow powder. Recrystallization from a water-ethanol mixture gave 17.6 g. (65% yield) of pale yellow crystals, m.p. 90°–93° C.

d) Intermediate compound (4): Synthesis of (6,6'-bis-[1-(3-amino-4-chloro-carbamoyl)-n-pentoxy]-4,4,4',4',7,7'-hexamethyl-2,2'-spirobichroman)

To a solution of 13.6 g. (0.015 mole) of the intermediate compound (3) in 120 ml. of ethyl acetate incorporated with 6.5 g. of iron powder was gradually added under reflux 25 ml. of a 90% acetic acid. The resulting mixture was allowed to undergo reaction for 12 hours under reflux. After filtering, the flitrate was concentrated under reduced pressure, and the residue was shaked together with benzene while heating, the benzene layer separated was washed several times with an aqueous hydrochloric acid solution and water and then dried over sodium sulfate. Concentration under reduced pressure gave white powder, and the white powder thus obtained was recrystallized from a mixed solvent of n-hexane and chloroform to obtain 9.9 g. (78% yield) of white crystals, m.p. 93°–96° C.

e) Synthesis of Exemplified compound (Y-4)

To a solution of 8.5 g. (0.01 mole) of the intermediate compound (4) in 60 ml. of xylene was added 10 g. of ethyl α-pivaloylacetate, and the mixture was heated under reflux. The mixture was placed in a distillation apparatus, and the ethanol formed under normal pressure and the solvent xylene were distilled off. The remaining mixture was further allowed to undergo reaction by heating at 150° C. for 3 hours. After distilling off an excess of ethyl α-pivaloylacetate under reduced pressure, the distillate was purified by means of silica gel column chromatography using a 3:1 mixture of n-hexane and acetone to obtain 9.3 g. (85% yield) of white crystals, m.p. 108°–112° C. According to NMR, IR and elementary analysis values as mesured, it was confirmed the white crystalline product thus obtained was the titled end product.

Elementary analysis for $C_{61}H_{78}Cl_2N_4O_{10}$: Calculated (%) C:66.73; H:7.11; N:5.10 Cl:6.47; Found (%) C:66.85; H:7.02; N:5.12; Cl:6.56;

SYNTHESIS EXAMPLE 5

Preparation of Exemplified compound (Y-5)

To a solution of 11 g. (0.01 mole) of the exemplified compound (Y-4) of Synthesis Example 4 in 150 ml. of chloroform was gradually added at 3°–7° C. a solution of 3 g. of sulfuryl chloride in 50 ml. of chloroform. The mixture was allowed to undergo reaction with stirring for 2 hours while maintaining the above-mentioned temperature range. After completion of reaction, the reaction liquid was concentrated under reduced pressure to obtain yellow powder. Recrystallization from ligroin gave 9.4 g. (81% yield) of pale yellow crystals, m.p. 123°–127° C. According to NMR, IR and elementary analysis values as measured, it was confirmed that the yellow crystalline product thus obtained was the end product.

Elementary analysis for $C_{61}H_{76}Cl_4N_4O_{10}$: Calculated (%) C:62.78; H:6.52; N:4.80; Cl:12.18; Found (%) C:62.63; H:6.64; N:4.68; Cl:12.31;

SYNTHESIS EXAMPLE 6

Preparation of Exemplified compound (Y-6)

A solution of 11.7 g. (0.01 mole) of the exemplified compound (Y-5) of Synthesis Example 5 in 150 ml. of acetonitrile was adjusted with triethylamine to pH 7-8, charged with 5.5 g. of 4-tolyl-tetrazolyl-5-one-potassium salt and then allowed to undergo reaction by heating under reflux for 3 hours. After completion of reaction, the deposited salt and an excess of 4-tolyl-tetrazolyl-5-one-potassium salt were separated by filtration, and the filtrate was concentrated under reduced pressure. The concentrated residue was dissolved in ethyl acetate, washed several times with an aqueous sodium carbonate solution, aqueous hydrochloric acid solution and water and then dried over sodium sulfate. Concentration under reduced pressure gave pale yellow powder. This powder was purified by means of silica gel column chromatography using a 3:1 mixture of n-hexane and acetone as a developing solvent to obtain 9.1 g. (63% yield) of pale yellow powder having an indistinct melting point in the vicinity of 140° C. According to NMR, IR and elementary analysis values as measured, it was confirmed that the pale yellow powdery product thus obtained was the titled end compound.

Elementary analysis for $C_{77}H_{90}Cl_2N_{12}O_{12}$: Calculated (%) C:63.94; H:6.23; N:11.63; Cl:4.91 Found (%) C:63.73; H:6.31; N:11.49; Cl:4.80;

SYNTHESIS EXAMPLE 7

Preparation of Exemplified compound (C-2)

a) Intermediate compound (1): Synthesis of (6,6'-bis-(3-cyanopropoxy-4,4,4',4',7,7'-hexamethyl-2,2'-spirobichroman)

A solution of 8.4 g. (0.36 mole) of metallic sodium in 300 ml. of absolute ethanol was charged with 44.2 g. (0.12 mole) of 6,6'-dihydroxy-4,4,4',4',7,7'-hexamethyl-2,2'-spirobichroman and further with 35.5 g. (0.24 mole) of γ-butyronitrile, and the resulting mixture was allowed to undergo-reaction by heating under reflux for 10 hours. Cooling overnight, the deposited crystals were collected and the salt formed was removed by water-washing. The crystals remained were recrystallized from ethanol to obtain 48.8 g. (81.0% yield) of prism-like crystals, m.p. 153°–154° C.

b) Intermediate compound (2): Synthesis of (6,6'-bis-(4-aminobutyloxy)-4,4,4',4',7,7'-hexamethyl-2,2'-spirobichroman)

To a dispersion of 7 g. of lithium aluminum hydride in 700 ml of absolute ether was gradually added dropwise with stirring a solution of 25.1 g. (0.05 mole) of the intermediate compound (1) in 100 ml of anhydrous dioxane. After a 3-hour reaction under reflux, the reaction liquid was carefully poured into water, thereby to decompose an excess of lithium aluminum hydride. The ethereal layer separated was dried over sodium sulfate. The solvent was concentrated under reduced pressure to obtain 24.5 g. (94% yield) of a colorless wax-like solid. This wax-like solid was used in the subsequent reaction without purification.

c) Synthesis of Exemplified compound (C-2)

A solution of 24 g. of the intermediate compound (2) and 24.9 g. of phenyl 1-hydroxynaphthoate in 30 ml. of benzene was gradually heated in a reactor equipped with a distillation apparatus. After distilling off the solvent, reaction was carried out under reduced pressure by heating at about 150° C. for 1 hour. After completion of reaction, the reaction product was cooled and washed with n-hexane to obtain a brown syrup-like product. This syrup-like product was purified by means of silica gel column chromatography using a 30:1 mixture of benzene and methanol as a developing solvent to obtain 21.2 g. (53% yield) of a pale yellow syrup-like product. According to NMR, IR and elementary analysis values as measured, it was confirmed that the syrup-like product thus obtained was the titled end product.

Elementary analysis for $C_{53}H_{58}N_2O_8$: Calculated (%) C:74.82; H:6.82; N:3.29; Found (%) C:74.61; H:6.93; N:3.40

SYNTHESIS EXAMPLE 8

Preparation of Exemplified compound (C-12)

A solution of 18 g. (0.03 mole) of the intermediate compound (2) of Synthesis Example 4 in 150 ml. of carbon tetrachloride was charged with 13.8 g. (0.066 mole) of phosphorus pentachloride and allowed to undergo reaction by heating under reflux for 1 hour. After cease of evolution of hydrochloric acid, phosphorus oxychloride formed during reaction and the solvent were distilled off to obtain a syrup-like acid chloride. A solution of this acid chloride in 150 ml. of acetonitrile was charged with 11.5 g. (0.06 mole) of 2-amino-4,6-dichloro-5-methylphenol and allowed to undergo reaction by heating under reflux for 3 hours. After completion of reaction, unreacted 2-amino-4,6-dichloro-5-methylphenol was separated by filtration. After concentration under reduced pressure, the residue was purified by means of silica gel column chromatograph using a 95:5 mixture of benzene and acetone to obtain 18.4 g. (65% yield) of white crystals, m.p. 109°–112° C. According to NMR, IR and elementary analysis values as measured, it was confirmed that the white crystalline compound thus obtained was the end product.

Elementary analysis for $C_{49}H_{56}Cl_4N_2O_8$: Calculated (%) C:62.29; H:6.14; N:2.97; Cl:15.04; Found (%) C:62.15; H:6.01; N:3.10; Cl:15.12

By virtue of introducing a group having antioxidation ability into any optional position of the molecular structure of coupler used in color photosensitive materials, as shown in the aforementioned general formula (I), the coupler of the present invention has particularly been successful not only in improving the resultant dye image in light fastness but also in preventing unexposed areas from Y-stain.

In addition to the above-mentioned effects, it was a surprise to find that the couplers of the present invention are excellently soluble in high boiling solvents, excellent in stability even when they are dispersed in a silver halide emulsion and do not throw any hinderance to color development, that light absorption wavelengths of the dyes obtained from the present couplers are found to be in their respective desirable ranges, and that the present couplers do not exert any detrimental influence on photographic properties of the color photosensitive materials using the same and the dye images formed thereby are excellent not only in light fastness but also excellent in fastness to heat and humidity.

In general, the couplers of the present invention are usually incorporated into silver halide emulsion layers of color photosensitive materials. In the case where the present couplers are used with the view of attaining an effect of preventing the formed dye images from fading, said couplers may be incorporated into any layer adjacent to the silver halide emulsion layers.

The couplers of the present invention are preferably incorporated, according to procedures disclosed in U.S. Pat. Nos. 2,322,027, 2,801,170, 2,801,171, 2,272,191 and 2,304,940, by dissolving them in high boiling solvents, if necessary, using low boiling solvents in combination therewith, and forming the resulting solutions into coupler dispersions. In that case, hydroquinone derivatives, ultraviolet absorbers, etc. may be freely usable, if necessary, in combination with such couplers, and the present couplers may also be usable in admixture of two or more. More particularly, one or two or more couplers of the present invention, if necessary, together with hydroquinone derivatives, ultraviolet absorbers, etc., are dissolved in such high boiling solvents as will be illustrated below, if necessary, using such low boiling solvents as will be mentioned hereinafter, the resulting solutions are mixed with an aqueous solution containing such hydrophilic binder as gelatin and such anion type surface active agent as alkylbenzenesulfonic acid or alkylnaphthalenesulfonic acid and/or nonion type surface active agent such as sorbitane sesquileate or sorbitane monolaurate, and the resulting mixture is subjected to a high speed rotary mixer, colloid mill or supersonic wave dispersion apparatus to obtain an emulsified dispersion which is then incorporated into silver halide emulsions. The high boiling solvents usable in the above case include, for example, organic acid amides, carbamates, esters, ketones, urea derivaties and the like, particularly di-n-butyl phthalate, tricresyl phosphate, triphenyl phosphate, di-isooctyl azelate, di-n-butyl sebacate, tri-n-hexyl phosphate, N,N-diethyl-caprylamide butyl, N,N-diethyl laurylamide, n-pentadecyl phenyl ether, di-octyl phthalate, n-nonylphenol, 3-pentadecyl ethyl ether, 2,5-di-sec-amylphenylbutyl ether, monophenyl-di-O-chlorophenyl phosphate and fluorinated parrafin, and the low boiling solvents include, for example, methyl acetate, ethyl acetate, propyl acetate, butyl acetate, butyl propionate, cyclohexanol, diethylene glycol monoacetate, nitromethane, carbon tetrachloride, chloroform, cyclohexanetetrahydrofuran, methyl alcohol, acetonitrile, dimethylformamide, dioxane and methyl ethyl ketone (these high boiling and low boiling solvents may be used either singly or in admixture thereof).

Of the couplers of the present invention, those which are in a liquid state at ordinary temperature or which are relatively low in melting point may be also usable as solvents for oil-soluble coupler compounds in place of a part or whole of the aforementioned high boiling solvent.

The amount of the present coupler to be incorporated is not limited, but is preferably 10 to 100 g. per mole of silver halide, and said amount may be suitably changed, if necessary.

Ultraviolet absorbers usable in combination with the couplers of the present invention include, for example, compounds of thiazolidone, benzotriazole, acrylonitrile and benzophenone types as disclosed in U.S. Pat. Nos. 2,739,888, 3,004,896, 3,253,921, 3,533,794, 3,692,525, 3,705,805, 3,738,837, 3,754,919, 3,052,636 and 3,707,375, and British Pat. No. 1,321,355. The use of these ultraviolet absorbers is of advantage to prevent the resulting dye images from fading due to actinic rays of shorter wavelength, and particularly the use, either singly or incombination, of Thinupin PS, 320, 326, 327 and 328 (products of Chiba-Geigy Co.) is of advantage.

Hydroquinone derivatives usable in combination with the couplers of the present invention include precursors thereof. By precursors as used herein are meant compounds which release hydroquinone derivatives on hydrolysis. Such precursors include, for example, such compounds in which one or two hydroxyl groups of hydroquinone nucleus have been converted, for example, into

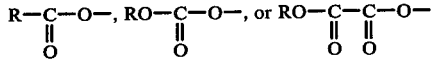

wherein R represents an aliphatic group such as alkyl or the like.

Representatives of the hydroquinone derivative used in the present invention include such compounds as represented by the following general formula (VIII).

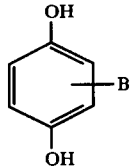

wherein B represents an alkyl group (e.g. methyl, t-butyl, t-amyl, octyl, t-octyl, dodecyl, octadecyl, etc.), an aryl group (e.g. phenyl, etc.), an alkoxy group (e.g. methoxy, butoxy, dodecyloxy, etc.), an aryloxy group (e.g. phenoxy, etc.), a carbamoyl group (e.g. methylcarbamoyl, dibutylcarbamoyl, octadecylcarbamoyl, phenylcarbamoyl, etc.), a sulfamoyl group (e.g. methylsulfamoyl, octadecylsulfamoyl, etc.), an acyl group (e.g. acetyl, octanoyl, lauroyl, etc.), an alkoxycarbonyl group (e.g. methoxycarbonyl, dodecyloxcarbonyl, etc.) or an aryloxycarbonyl group (e.g. phenyloxycarbonyl, etc.), and the alkyl moiety as well as the aryl moiety in the above-mentioned groups may include those substituted with such substituent as halogen, alkyl, aryl, alkoxy, aryloxy, carboxy, alkoxycarbonyl, aryloxycarbonyl, acyl, acyloxy, carbamoyl, sulfo, sulfamoyl, sulfonamido, N-alkylamino, N-arylamino, acylamino, imido or hydroxy group, and one to three out of the remaining three hydrogen atoms on an aromatic nucleus of the hydroquinone may be substituted by halogen atoms and one to three (may be the same or different) out of the groups defined as the B substituents.

Examples of the nuclearly substituted hydroquinones used in the present invention are exemplified, for example, in U.S. Pat. Nos. 2,336,327, 2,360,290, 2,384,658, 2,403,721, 2,418,613, 2,675,314, 2,701,197, 2,704,713, 2,710,801, 2,722,556, 2,728,659, 2,732,300, 2,735,765, 2,816,028, 3,062,884 and 3,236,896, British Patents 557,750 and 557,802, West German Patent Publication No. 2,149,789, Japanese Patent Publication No. 54116/1969, Japanese Laid-Open-to-Public Publication No. 2128/1971, and Journal of Organic Chemistry, Vol. 22, PP. 772–774.

Of the nuclearly substituted hydroquinone derivatives, those which have carbon atoms contained in the substituents on the nucleus and amounting to 8 or more are low in diffusibility and suitable for being selectively made present in a specific hydrophilic layer of photosensitive material.

Of the hydroquinone derivatives, those which have substituted or unsubstituted alkyl as the substituents on the nucleaus are particularly useful.

Listed below are examples of the hydroquinone derivative used in the present invention, but those are construed as illustrative and not limitative.

| | |
|---|---|
| Hq - 1 | 2,5-di-tert-Octylhydroquinone |
| Hq - 2 | 2-tert-Octyl-5-methylhydroquinone |
| Hq - 3 | 2,6-di-n-Dodecyl-hydroquinone |
| Hq - 4 | 2-n-Dodecylhydroquinone |
| Hq - 5 | 2,2'-Methylenebis-5,5'-di-t-butylhydroquinone |
| Hq - 6 | 2,5-di-n-Octyl-hydroquinone |
| Hq - 7 | 2-Dodecylcarbamoylmethylhydroquinone |
| Hq - 8 | 2-(β-n-Dodecyloxycarbonyl)ethyl-hydroquinone |
| Hq - 9 | 2-(N,N-Dibutylcarbamoyl)hydroquinone |
| Hq - 10 | 2-n-Dodecyl-5-chloro-hydroquinone |
| Hq - 11 | 2-(2-Octadecyl)-5-methylhydroquinone |
| Hq - 12 | 2,5-di-(p-Methoxyphenyl)hydroquinone |
| Hq - 13 | 2-tert-Octylhydroquinone |
| Hq - 14 | 2-[β-{3-(3-Sulfobenzamido)benzamido}-ethyl]hydroquinone |
| Hq - 15 | 2,5-Dichloro-3,6-diphenylhydroquinone |
| Hq - 16 | 2,6-Dimethyl-3-tert-octylhydroquinone |

| | |
|---|---|
| Hq - 17 | 2,3-Dimethyl-5-tert-octylhydroquinone |
| Hq - 18 | 2-{β- (Dodecanoyloxy)ethyl}carbamoylhydroquinone |
| Hq - 19 | 2-Dodecyloxycarbonylhydroquinone |
| Hq - 20 | 2-{β-(4-Octanamidophenyl)ethyl}hydroquinone |
| Hq - 21 | 2-Methyl-5-dodecylhydroquinone |

The above-listed hydroquinone derivatives are either singly or in combination of two or more, and the amount of said derivative to be incorporated is usually preferably 0.01 to 10 moles, particularly preferably 0.1 to 3 moles, per mole of a coupler present in the coupler containing color photosensitive material.

Silver halide emulsions used in the color photosensitive material according to the present invention are generally emulsions prepared by dispersing silver halide particles in a hydrophilic colloid. The silver halide includes silver chloride, silver bromide, silver iodide, silver chlorobromide, silver chloroiodobromide and the mixtures thereof. These silver halides are prepared by various procedures such as ammonia process, neutral process, a so-called conversion process and simultaneous mixing process. The hydrophilic colloid, in which the silver halide is dispersed, includes in gelatin and gelatin derivatives such as phthalated gelatin and malonated gelatin. In place of a part or whole of this gelatin and such gelatin derivatives, there may also be used albumin, agar, gum arabic, alginic acid, casein, partially hydrolyzed cellulose derivatives, polyvinyl alcohol, partially hydrolyzed polyvinyl acetate, polyacrylamide, imidated polyacrylamide, polyvinylpyrrolidone and copolymers of these vinyl compounds. Further, the silver halide emulsions may be subjected to chemical sensitization using various kinds of sensitizing dyes in order to impart sensitivity at a desired sensitive wavelength region. Preferable sensitizing dyes include cyanine dyes, merocyanine dyes or composite cyanine dyes, which may be used either singly or in combination, disclosed, for example, in U.S. Pat. Nos. 1,939,201, 2,072,908, 2,688,545, 2,739,149, 2,912,329, 2,213,995, 2,493,748, 2,519,001, 3,397,060 and 3,628,964, West German Pat. No. 1,242,588, British Pat. Nos. 1,195,302, 1,242,588, 1,293,862 and 505,979, West German Patent Publication Nos. 2,030,326 and 2,121,780, Japanese Patent Publication Nos. 4936/1968 and 14030/1969. If necessary, moreover, the emulsions may be used after being incorporated with various photographic additives which may be used either singly or in combination. These photographic additives include, for example, chemical sensitizing agents such as gold compounds, noble metal salts of platinum, palladium, iridium, rhodium, ruthenium and the like, sulfur compounds, reducing substances or thioether compounds, quaternary ammonium salt compounds or polyalkyleneoxide compounds, stabilizing agents such as triazoles, imidazoles, azaindenes, benzothiazolium compounds, zinc compounds, cadmium compounds and mercaptans, chromium salts, zirconium salts and mucochloric acid disclosed in U.S. Pat. Nos. 1,574,944, 2,399,083, 2,410,689, 2,448,060, 2,487,850, 2,518,698, 2,521,925, 2,521,926, 2,540,085, 2,540,086, 2,566,245, 2,566,263, 2,597,856, 2,597,915, 2,598,079, 2,983,610, 3,189,458, 3,201,254 and 3,501,313; film hardening agents including those of aldehyde type, triazine type, polyepoxy compounds, active halogen compounds, ketone compounds, acryloyl type, triethylenephosphamide type and of ethyleneimine type; plasticizers such as glycerin and 1,5-pentanediol; fluorescent brightening agents; antistatic agents and coating aids disclosed in Japanese Patent Publication Nos. 7133/1959 and 1872/1971, British Pat. Nos. 686,440, 974,732, 994,869 and 1,332,647, U.S. Pat. Nos. 682,641, 2,725,295, 2,732,303, 2,732,316, 2,983,611, 3,017,280, 3,091,537, 3,100,704, 3,103,437, 3,321,313, 3,325,287, 3,362,827, 3,543,292, 3,635,718 and 3,736,320.

The emulsion prepared in the manner explained above is incorporated with a dispersion prepared by dispersing therein the couplers, etc. according to the present invention as aforesaid and then coated on a support such as a film of such synthetic resin as cellulose acetate, cellulose nitrate, polycarbonate, polyethylene terephthalate or polystyrene, baryta paper, polyethylene-coated paper or glass plate, if necessary through a sub layer, antihalation layer, intermediate layer, yellow filter layer and protective layer provided on the support, whereby to obtain a color photosensitive material. The color photosensitive material according to the present invention may comprise therein not only one layer of a silver halide emulsion layer but also two or more layers of silver halide emulsion layers, and may also comprise two or more emulsion layers which are sensitive at the same wavelength region.

The color photosensitive material according to the present invention is a coupler containing internal type color photosensitive material and, after exposure, is advantageously color developed according to color development method. The present color photosensitive material may be usable as a color photosensitive material in which both couplers and a color developing agent are made present in the same one layer and are individually protected so that they may not be brought into contact with each other at the time before exposure but may be brought into contact with each other after exposure, or as a color photosensitive material in which a color developing agent is made present in a layer containing no couplers and said color developing agent is allowed, when an alkaline processing solution is permeated into said layer, to move in a layer containing the coupler so that said color developing agent may be brought into contact with said coupler. When the present color photosensitive material is used as a color photosensitive material for diffusion transfer, the couplers of the present invention may be used by incorporating them into a light-sensitive element and/or an image-receiving element of said photosensitive material, and particularly the present couplers are advantageously made present in the light-sensitive element. In the case of reversal development, the present color photosensitive material, after exposure, is developed with a black-and-white negative developer, followed by exposure to white light or treatment with a bath containing such fogging agent as a boron compound, and is then color developed with an alkaline developer containing a color developing agent. In that case, the fogging agent may be incorporated into the alkaline developer containing the color developing agent. After color development, the photosensitive material is subjected to bleaching treatment with a bleaching solution containing, as an oxidizing agent, ferricyanide or ferric salt of aminopolycarboxylic acid and is then subjected to fixing treatment with a fixing solution containing a silver salt dissolving agent such as thiosulfate or the like, thereby to remove a silver image and the remaining silver halide and leave a dye image. It is also possible to effect bleach-fixing of the developed photosensitive material by the use of a one bath bleach-fixing solution containing an oxidizing agent such as ferric salt of aminocarboxylic acid and a silver salt dissolving agent such as thiosulfate in place of the use of the bleaching solution and then of the fixing solution. It is also possible to subject the exposed photosensitive material to such treatments as pre-hardening, neutralizing water-washing, stopping and stabilizing in combination with color development, bleaching, fixing or bleach-fixing treatment. A processing step wherein the color photosensitive material according to the present invention is particularly advantageously subjected to development treatment is, for example, a sequence of steps of color development, if necessary, water-washing, bleach-fixing, water-washing, and stabilizing and dyring, if necessary, and this processing step may be carried out at elevated temperature, for example, above 30° C. and with a quite short time.

Particularly useful color developing agents used in color developing the color photosensitive materials according to the present invention are primary phenylenediamines and aminophenols and derivatives thereof. Typical examples of the color developing agents include, for example, those as enumerated below.

N,N-Dimethyl-p-phenylenediamine, N,N-diethyl-p-phenylenediamine, n-carbamidomethyl-N-methyl-p-phenylenediamine, N-carbamidomethyl-N-tetrahydrofurfuryl-2-methyl-p-phenylenediamine, N-ethyl-N-carboxymethyl-2-methyl-p-phenylenediamine, N-carbamidomethyl-N-ethyl-2-methyl-p-phenylenediamine, N-ethyl-N-tetrahydrofurfuryl-2-methyl-p-aminophenol, 3-acetylamino-4-aminodimethylaniline, N-ethyl-N-$\beta$-methanesulfonamidoethyl-4-aminoaniline, N-ethyl-N-$\beta$-methanesulfonamidoethyl-3-methyl-4-aminoaniline, N-methyl-N-$\beta$-sulfoethyl-p-phenylenediamine, o-aminophenol, p-aminophenol, and salts of 5-amino-2-oxy-toluene with such inorganic acid as hydrochloric or sulfuric acid or such organic acid as p-toluenesulfonic acid.

The color developing solution is incorporated, in addition to the color developing agent as aforesaid, with various additives. Principal examples of such additives include, for example, hydroxides of alkali metals or ammonium, alkali agents such as phosphates, buffers such as acetic or boric acid, pH regulators, development accelerators, antifoggants, stain or sludge preventing agents, multi-layer effect promoting agents and constant state maintaining agents.

The bleaching agents used in bleaching treatment include ferricyanide such as potassium ferricyanide, bichromates, permanganates, hydrogen peroxide, bleaching powder, metal complex salts of aminopolycarboxylic acid such as ethylenediaminetetraacetic acid, nitrotriacetic acid, iminodiacetic acid, etc., metal complex salts of polycarboxylic acid such as malonic acid, tartaric acid, malic acid, diglycolic acid, etc., and ferric chloride, and these bleaching agents may be used singly or, if necessary in combination therewith. The bleaching solution may be incorporated, if necessary, with various additives such as bleaching promotors and the like.

The fixing agents used in fixing treatment include thiosulfates such as sodium thiosulfate, ammonium thiosulfate, etc., cyanides, and urea derivatives, and the fixing solution may be incorporated, if necessary, with various additives such as fixing promotors and the like.

Color photosensitive materials in which the couplers of the present invention have been used may also be advantageously processed by the solution containing both a primary aromatic amine type color developing agent and an oxidizing agent capable of allowing a metallic silver image to undergo redox reaction.

When the above-mentioned color developing solution is used in developing the exposed color photosensitive material, the color developing agent is oxidized by means of the oxdizing agent and the oxidized color developing agent undergoes coupling with couplers to form a dye image. Such color developing solution is disclosed, for example, in Japanese-Laid-Open-to-Public Publication No. 9729/1973, and an oxidizing agent preferably suitable for the purpose includes cobalt complex salts having a coordination number of 6. Color photographic treatment involving the use of such color developing solution as mentioned above is particularly effectively applicable to processing of the so-called silver-saving type color photosensitive materials in which the amount of silver used is smaller than that of ordinary color photosensitive materials.

Particularly advantageously useful cobalt complex salts are those which contain ligands selected from the group consisting of ethylenediamine, diethylenetriamine, triethylenetetramine, amine, nitrate, nitrite, azide, chloride, thiocyanate, isothiocyanate, water and carbonate and which have (1) at least two ethylenediamine ligands, (2) at least five amine ligands or (3) at least one triethylenetetramine ligand. Particularly preferable cobalt complex salts are such complex salts as represented, for example, by the following formulas.

$[CO(En)_2(N_3)_2]X$; $[CO(En)_2Cl(NCS)]X$;

$[CO(En)_2(NH_3)N_3]X$; $[CO(En)_2Cl_2]X$;

$[CO(En)_2(SCN)_2]X$; $[CO(En)_2(NCS)_2]X$;

and $[CO(NH_3)_6]X$.

In the above formulas, En represents ethylenediamine and X represents at least one anion selected from chloride, bromide, nitrite, nitrate, perchlorate, acetate, carbonate, sulfite, sulfate, hydrochloride, thiocyanate, isothiocyanate and hydroxide. Most preferable complex salts are hexamine salts of cobalt, for example, chlorides, bromides, sulfites, sulfates, perchlorates, nitrites and acetates. The cobalt complex salt is generally used in a concentration ranging from about 0.1 to 50 g. per liter of the color developing solution.

Color photosensitive materials having contained therein the couplers of the present invention are advantageously applicable also to a photographic processing process which comprises developing the exposed color photosensitive material in a color developing solution containing an aromatic primary amine type color developing agent, preferably in the presence of such color developing agent as may be received during color developing step into a photosensitive layer and as may be allowed to move into an amplifying bath, and then contacting the developed color photosensitive material with an amplifying solution containing the aforesaid oxidizing agent, for example, a cobalt complex salt having a coordination number of 6. Further, preferably usable as other oxidizing agent suitable for this purpose is an aqueous hydrogen peroxide solution disclosed, for example, in Japanese Laid-Open-to-Public Publication No. 16023/1976. It is preferable that this amplifying solution is incorporated, in addition to the oxidizing agent, with a development inhibitor for silver halide and then used in processing color photosensitive materials. In such case, the amplifying step can be carried out in an illuminated room. According to this technique, it becomes possible to observe the progress of formation of dye and the dye formation can be suspended after a desired dye density has been attained. Preferable development inhibitors are water-soluble bromide compounds, such as potassium bromide, and heterocyclic compounds such as tetrazoles, azaindenes and triazoles containing no mercapto or ionic bromide group.

A concentration of the cobalt complex salt to be contained in the amplifying solution is generally about 0.2 to about 20 g/l, most preferably about 1 to about 15 g/l, and that of the aqueous hydrogen peroxide solution is generally about 0.01 to 10%, most preferably 0.5 to 10%. In case, the water-soluble bromide compound is used as a development inhibitor in the amplifying solution, said compound is contained therein generally in an amount of about 1 to about 40 g/l. The development inhibitor consisting of a compound having a heterocyclic structure, on the other hand, is used usually in a concentration of about 0.01 to about 3 g/l. The amplifying solution, when used, is ordinarily adjusted to pH 6-14, preferably pH 8-12.

Further, if necessary, the amplifying solution may be incorporated with development accelerators, stabilizers, water-softening agents, thickners, uneven treatment preventing agents and the like additives in addition to the above-mentioned development inhibitors.

The present invention is illustrated below with reference to examples, but embodiments of the invention are not limited by these examples.

EXAMPLE 1

Couplers (M-1), (M-3) and (M-7), comparative couplers A, B and C, and a combination of the comparative coupler A and a fading inhibitor were individually dissolved together with 120 mg. of Hq - 1 in a mixture of dibutyl phthalate (DBP) and ethyl acetate (EA) in the manner as shown in Table 1 - 1. Each of the resulting solution was incorporated into a mixture comprising 100 ml. of an aqueous solution of sodium dialkylnaphthalenesulfonate (Alkanol B: a product produced and sold by Du Pont Co.) and 400 ml. of a 5% aqueous gelatin solution, and the resulting mixture was emulsified and dispersed by means of a colloid mill to obtain a coupler dispersion. Subsequently, each of the coupler dispersions obtained in the above manner was incorporated into 1000 ml. of a green-sensitive silver chlorobromide emulsion (containing 40 mole% of silver chloride). The emulsion was charged with 20 ml. of a 1% aqueous solution of 1,2-bis(vinylsulfonyl)ethane as a film hardener, coated on a polyethylene-coated paper and then dried. In this manner, there were obtained sample Nos. 1 to 7 of color photosensitive materials.

After exposure to light through an optical wedge, the samples were individually processed at 30° C. according to the following procedure to obtain samples having formed thereon their respective color images.

Processing step:

Color development (3 min. 30 sec.) → bleach-fixing (1 min. 30 sec.) → water-washing (2 min.) → stabilizing (1 min.) → drying. The processing solutions used in the processing step were such as having the following compositions:

Composition of the color developing solution:

| | | |
|---|---|---|
| Benzyl alcohol | 5.0 | ml |
| Sodium metaphosphate | 2.5 | g |
| Anhydrous sodium sulfite | 1.9 | g |
| Sodium bromide | 1.4 | g |
| Potassium bromide | 0.5 | g |
| Borax (Na$_2$B$_4$O$_7$ . 10 H$_2$O) | 39.1 | g |
| N-Ethyl-N-β-methanesulfonamidoethyl-4-aminoaniline sulfate | 5.0 | g |
| Water to make 1 liter and adjust the pH to 10.30 with sodium hydroxide. | | |

Composition of the bleach-fixing solution:

| | | |
|---|---|---|
| Ammonium iron ethylenediaminetetraacetate | 61.0 | g |
| Diammonium ethylenediaminetetraacetate | 5.0 | g |
| Ammonium thiosulfate | 124.5 | g |
| Sodium metabisulfite | 13.3 | g |
| Water to make 1 liter and adjust to pH 6.5 with ammonia water. | | |

Composition of the stabilizing solution:

| | |
|---|---|
| Glacial acetic acid | 20 ml |
| Add 800 ml. of water and adjust to pH 3.5-4.0 with sodium acetate and then water to make 1 liter. | |

Each of the samples thus processed was measured in speed, gamma, fog and maximum density. In order to investigate light fastness of each sample, moreover, a density after irradiation for 100 hours by means of a xenon fade-o-meter as measured in terms of residual dye ratio, when the initial density was 1.0, was obtained and, further, a density after the irradiation in the unexposed area of each sample as measured in terms of Y-stain increasing ratio represented by percent was obtained. The results obtained were as shown in Table 1 - 2.

In the table, the speed was represented by a relative value as measured by assuming as 100 the speed of the sample in which the comparative coupler A was used singly.

Table 1 - 1

| Sample No. | Exemplified compound | Amount of compound added (g) | DBP (g) | EA (g) |
|---|---|---|---|---|
| 1 | (M - 1) | 31.5 | 32 | 100 |
| 2 | (M - 3) | 36.0 | 36 | " |
| 3 | (M - 7) | 40.0 | 40 | " |
| 4 | Comparative coupler - A | 35.5 | 36 | " |
| 5 | Comparative coupler - A | 35.5 | 36 | " |
|   | Fading inhibitor | 10.5 | | |
| 6 | Comparative coupler - B | 40.0 | 40 | " |
| 7 | Comparative coupler - C | 37.0 | 37 | " |

Table 1 - 2

| Sample No. | Speed | Fog | Gamma | Maximum density | Residual dye ratio (%) | Y-stain increasing ratio (%) |
|---|---|---|---|---|---|---|
| 1 | 102 | 0.02 | 2.4 | 2.8 | 83 | 460 |
| 2 | 105 | 0.02 | 2.3 | 2.7 | 88 | 420 |
| 3 | 101 | 0.02 | 2.4 | 2.7 | 90 | 410 |
| 4 | 100 | 0.03 | 2.5 | 2.8 | 55 | 1200 |
| 5 | 99 | 0.02 | 2.5 | 2.7 | 65 | 660 |
| 6 | 92 | 0.02 | 2.3 | 2.6 | 78 | 600 |

Table 1 - 2-continued

| Sample No. | Speed | Fog | Gamma | Maximum density | Residual dye ratio (%) | Y-stain increasing ratio (%) |
|---|---|---|---|---|---|---|
| 7 | 100 | 0.03 | 2.4 | 2.8 | 64 | 845 |

The comparative couplers and fading inhibitor used were those having the following their respective structures.

Comparative coupler A:

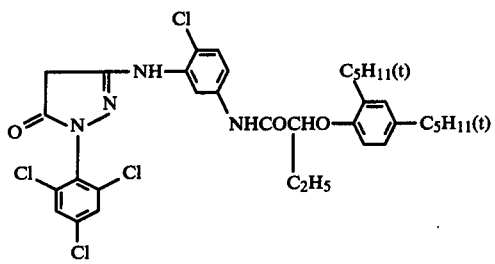

Comparative coupler B:

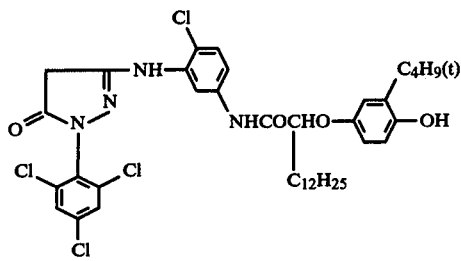

(A compound disclosed in U.S. Pat. No. 3,519,429)

Comparative coupler C:

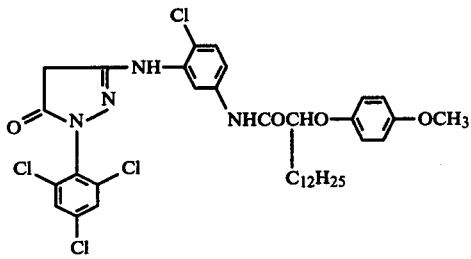

(A compound disclosed in Japanese Laid-Open-to-Public Publication No. 20723/1975)

Fading inhibitor:

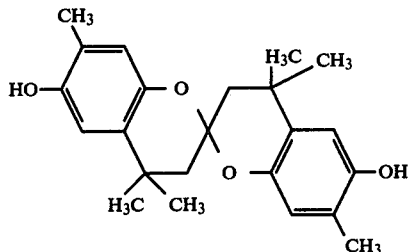

(A compound disclosed in Japanese Patent Publication No. 20977/1974)

From the results shown in Table 1 - 2, it is understood that the couplers of the present invention have excellent fading inhibition effect as well as Y-stain prevention effect, as compared with the known couplers.

Further, the present couplers were excellent not only in solubility in such highboiling solvent as DBP but also in stability to dispersions in which they had been dispersed.

EXAMPLE 2

Each of couplers (Y-4) and (Y-6) of the present invention and comparative couplers D and E which will be illustrated later was dissolved together with 150 mg. of Hq - 1 in each of the mixed solvents shown in Table 2 - 1. The resulting solution was incorporated into 500 ml. of a 5% aqueous gelatin solution containing 3.0 g of sodium dodecylbenzenesulfonate, and the mixture was then dispersed by means of a homogenizer to obtain a dispersion. The dispersion thus obtained was incorporated into 1000 ml. of a blue-sensitive silver chlorobromide emulsion (containing 10 mole% of silver chloride), and the resulting emulsion was charged with 10 ml. of a 2% methanol solution of N,N',N''-trisacryloyl-hexahydro-S-triazine as a film hardener, coated on a subbed polyethylene terephthalate film and then dried to obtain a sample. In this manner, there were obtained sample Nos. 1-4 of color photosensitive materials which were then processed according to the following processing step.

Processing step:

Color development (at 30° C. for 3 min. 30 sec.) → stopping → first fixing → water-washing (10 min.) → bleaching (at 20° C. for 5 min.) → water-washing (at 20° C. for 5 min.) → second fixing (at 20° C. for 5 min.) → water-washing (at 20° C. for 25 min.) → drying.

A color developing solution used was such as having the same composition as in the solution used in Example 1 and the stopping and the first fixing were conducted according to the usual procedure.

Composition of the bleaching solution:

| Potassium ferricyanide | 100 g |
| Potassium bromide | 50 g |
| Water to make | 1 liter |

Composition of the fixing solution:

| Sodium thiosulfate (pentahydrate) | 250 g |
| Anhydrous sodium sulfite | 12 g |
| Potassium alum | 15 g |
| Acetic acid | 12 g |
| Water to make | 1 liter |

The samples thus processed were individually tested in the same manner as in Example 1, except that fog after the irradiation was measured but the measurement of Y-stain increasing ratio was omitted. The results obtained were as shown in Table 2 - 2.

Table 2 - 1

| Sample No. | Exemplified compound | Amount of compound added (g) | TCP (g) | EA (g) |
|---|---|---|---|---|
| 1 | (Y - 4) | 54 | 54 | 110 |
| 2 | (Y - 6) | 43 | 73 | " |
| 3 | Comparative coupler - D | 57 | 57 | " |
| 4 | Comparative coupler - E | 67 | 67 | " |

TCP: Tricresyl phosphate

Table 2 - 2

| Sample No. | Speed | Gamma | Fog | Maximum density | Residual dye ratio (%) | Fog after irradiation |
|---|---|---|---|---|---|---|
| 1 | 104 | 2.0 | 0.24 | 2.4 | 90 | 0.22 |
| 2 | 105 | 2.1 | 0.23 | 2.5 | 91 | 0.12 |
| 3 | 100 | 2.0 | 0.36 | 2.3 | 80 | 0.32 |
| 4 | 110 | 2.0 | 0.42 | 2.4 | 30 | 0.37 |

In Table 2 - 2, the speed was represented by a relative value as measured by assuming as 100 the speed of the sample containing the comparative coupler D.

The comparative couplers used were such compounds as having the following structures thereof.

Comparative coupler D:

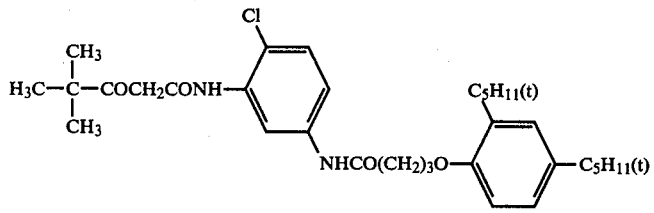

(A compound disclosed in U.S. Pat. No. 3,265,506)

Comparative coupler E:

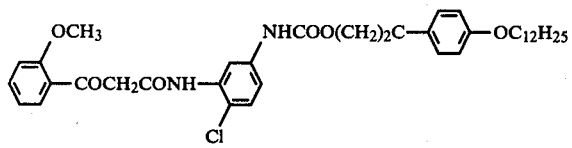

(A compound disclosed in Japanese Laid-Open-to-Public Publication No. 20723/1975)

From the results shown in Table 2 - 2, it is understood that the yellow couplers of the present invention also have excellent light fastness as compared with the conventionally known couplers and, at the same time, the present couplers are less in formation of the initial fog, cause no substantial damage in photographic properties of the resulting color photosensitive materials, have excellent solubility even in such high boiling solvent as TCP, and are excellent in stability to the dispersions in which they had been dispersed.

EXAMPLE 3

Each of couplers (C-2) and (C-12) of the present invention and comparative couplers, F, G, H and I was dissolved together with 1200 mg. of Hq - 1 in each of the mixed solvents in the manner as shown in Table 3 - 1. The resulting solution was incorporated into 500 ml. of a 5% aqueous gelatin solution containing sodium dodecylbenzenesulfonate and then dispersed by means of a homogenizer to obtain a dispersion. The dispersion was incorporated into 1000 ml. of a red-sensitive silver chlorobromide emulsion (containing 20 mole% of silver chloride), and the emulsion was charged with 20 ml. of a 4% aqueous solution of sodium 2,4-dichloro-6-hydroxy-S-triazine as a film hardener. Thereafter, the emulsion was coated on a subbed cellulose triacetate film and then dried to obtain a sample. In this manner, there were obtained sample Nos. 1-6 of color photosensitive materials.

The samples were individually processed and measured in exactly the same manner as in Example 1 to obtain the results in Table 3 - 2.

Table 3 - 1

| Sample No. | Exemplified compound | Amount of compound added (g) | TCP (g) | EA (g) |
|---|---|---|---|---|
| 1 | (C - 2) | 43 | 43 | 120 |
| 2 | Comparitive coupler - F | 47.5 | 46 | " |
| 3 | Comparitive coupler - G | 52 | 52 | " |
| 4 | (C - 12) | 47 | 47 | " |
| 5 | Comparitive coupler - H | 49 | 49 | " |
| 6 | Comparitive coupler - I | 57 | 57 | " |

Table 3 - 2

| Sample No. | Speed | Gamma | Fog | Maximum density | Residual dye ratio (%) | Y-stain increasing ratio (%) |
|---|---|---|---|---|---|---|
| 1 | 115 | 1.2 | 0.08 | 2.2 | 94 | 125 |
| 2 | 100 | 1.1 | 0.12 | 2.0 | 90 | 220 |
| 3 | 105 | 1.1 | 0.13 | 2.1 | 91 | 200 |
| 4 | 110 | 1.9 | 0.05 | 2.5 | 92 | 150 |
| 5 | 100 | 1.8 | 0.08 | 2.3 | 84 | 170 |
| 6 | 103 | 1.8 | 0.06 | 2.4 | 86 | 165 |

In the above table, the speed was represented by a relative value as measured by assuming as 100 the speed of the samples containing the comparative couplers F and H, respectively.

The comparative couplers used were such compounds as having their respective structures mentioned below.

Comparative coupler F:

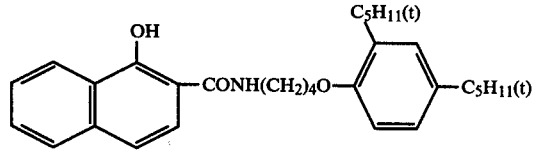

Comparative coupler G:

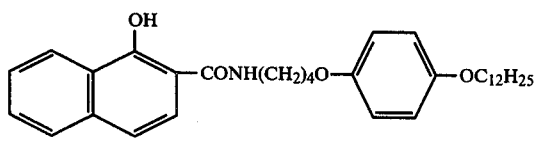

(A compound disclosed in Japanese Laid-Open-to-Public Publication No. 20723/1975)

Comparative coupler H:

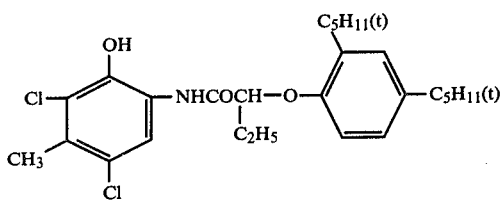

Comparative coupler I:

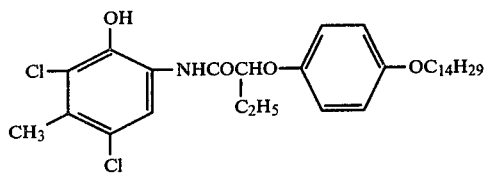

(A compound disclosed in Japanese Laid-Open-to-Public Publication No. 20723/1975)

From the results shown in Table 3 - 2, it is understood that when compared with the conventionally known couplers, the cyan couplers of the present invention also have excellent light fastness and, at the same time, are small in Y-stain increasing ratio. Furthermore, the present cyan couplers also have excellent solubility in high boiling solvents such as TCP and the like and are excellent in stability to the dispersions in which they had been dispersed.

Further, similar results to those in this example were obtained even when the hydroquinone derivatives Hq - 3, Hq - 5, Hq - 10, Hq - 13, Hq - 17 and Hq - 20 were used respectively in place of the Hq - 1 used in this example.

EXAMPLE 4

On a polyethylene-coated paper support were coated the under-mentioned layers successively in the following order from the side of the support surface to prepare a sample of color photosensitive material.
(Sample No. 1)

First layer: The first layer is a blue-sensitive silver halide emulsion layer comprising a silver chlorobromide emulsion containing 10 mole% of silver chloride, said emulsion containing 400 g. of gelatin per mole of silver halide, being sensitized by using $2.5 \times 10^{-4}$ mole, based on 1 mole of silver halide, of a sensitizing dye of the following structure, containing $1 \times 10^{-1}$ mole, based on 1 mole of silver halide, of the yellow coupler (Y-9) of the present invention dissolved and dispersed in dibutyl phthalate, and being coated on the support so that the amount of silver becomes 400 mg/m².

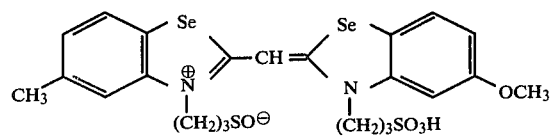

Second layer: The second layer is a gelatin layer coated on the first layer so as to have a dry film thickness of 1 micron.

Third layer: The third layer is a green-sensitive silver halide emulsion layer comprising a silver chlorobromide emulsion containing 40 mole% of silver chloride, said emulsion containing 500 g. of gelatin per mole of silver halide, being sensitized by using $2.5 \times 10^{-4}$ mole, based on 1 mole of silver halide, of a sensitizing dye of the following structure, containing $1 \times 10^{-1}$ mole, based on 1 mole of silver halide, of the magenta coupler (M-7) of the present invention dissolved and dispersed in tricresyl phosphate, and being coated on the second layer so that the amount of silver becomes 500 mg/m².

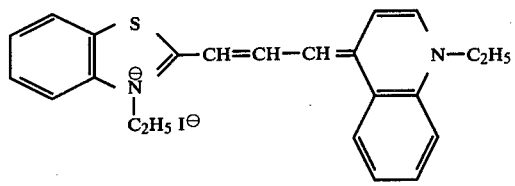

Fourth layer: The fourth layer is a gelatin layer containing di-t-octylhydroquinone dissolved and dispersed in dibutyl phthalate in a proportion of 30 mg/m² together with 2-(2'-hydroxy-3',5'-di-t-butylphenyl)benztriazole in a proportion of 0.7 g/m² and having a dry film thickness of 1 micron.

Fifth layer: The fifth layer is a red-sensitive silver halide emulsion layer comprising a silver chlorobromide emulsion containing 20 mole% of silver chloride, said emulsion containing 500 g. of gelatin per mole of silver halide, being sensitized by using $2.5 \times 10^{-4}$ mole, based on 1 mole of silver halide, of a sensitizing dye of the following structure, containing $1 \times 10^{-1}$ mole, base on 1 mole of silver halide, of the cyan coupler (C-12) of the present invention and being coated on the fourth layer so that the amount of silver becomes 500 mg/m².

Sixth layer: The sixth layer is a gelatin layer coated on the fifth layer so as to have a dry film thickness of 1 micron.

Each of the silver halide emulsions used in the above-mentioned photosensitive layers was prepared according to a procedure described in Japanese Patent Publication No. 7772/1971, sensitized chemically by using sodium thiosulfate pentahydrate and incorporated with 4-hydroxy-6-methyl-1,3,3a,7-tetrazaindene as a stabilizer, tetrakis-(vinylsulfonylmethyl)methane as a hardener and saponin as a coating aid.

Subsequently, a sample (No. 2) of a color photosensitive material was prepared in exactly the same manner as above, except that a known coupler of the following structure was used in place of the present coupler used in the first layer, the comparative coupler B used in Example 1 was used in place of the present coupler used in the third layer, and the comparative coupler H used in Example 3 was used in place of the present coupler used in the fifth layer, the molar quantity of each of said couplers used being twiced.

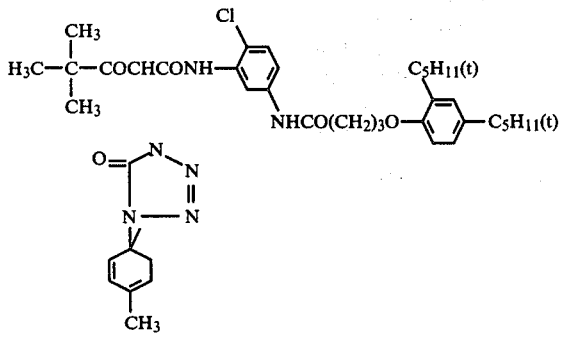

Each of the samples thus prepared was exposed through an optical wedge to blue light, green light and red light, respectively, and was then processed according to the procedure employed in Example 1. Thereafter, each sample was irradiated for 100 hours by means of a xenon fade-o-meter to measure its residual dye ratio and Y-stain increasing ratio to obtain the results as shown in Table 4, the measured values shown in said table being represented by the same manner as in Table 1 - 2 of Example 1.

Table 4

| Sample No. | Residual dye ratio(%) | | | Y-stain increasing ratio (%) |
| --- | --- | --- | --- | --- |
| | Yellow | Magenta | Cyan | |
| 1 | 94 | 96 | 97 | 140 |
| 2 | 90 | 88 | 95 | 280 |

From the results shown in Table 4, it is understood that the sample No. 1 containing the couplers of the present invention has excellent fading inhibition effect and Y-stain prevention effect as compared with the sample No. 2 containing the conventionally known couplers.

What we claim is:

1. A color photosensitive material comprising a support and a silver halide photosensitive layer which material contains a compound represented by the following formula:

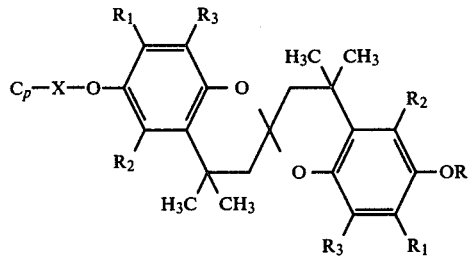

wherein $C_p$ represents a coupler residue bonded to the non-coupling position or is a magenta coupler bonded to the coupling position, $R_1$, $R_2$ and $R_3$ individually represent hydrogen, halogen, an alkyl group, an alkenyl group, an aryl group, an alkoxy group, an alkenyloxy group, an aryloxy group, an alkylthio group, an alkenylthio group, an arylthio group, an acyl group, an acylamino group, a diacylamino group, an acyloxy group, a sulfonamido group, alkylamino group, a cycloalkyl group, or an alkoxycarbonyl group, R represents hydrogen, an alkyl group, an alkenyl group, a cycloalkyl group, an aryl group, a heterocyclic ring selected from the group consisting of pyridinyl, pyradinyl, pyridadinyl, quinonyl, thienyl, piperidyl, pyrolyl, pyrrolinyl, tetrazolyl, thiadinyl, imidazolyl, morpholino, furyl, thiazolyl, oxazolyl, benzthiazolyl, benzoxazolyl, benzimidazolyl and furanyl, an acyl group, a carbamoyl group, thiocarbamoyl group, a sulfamoyl group, or $C_p$—X—, and X represents a simple bond, or a divalent group selected from the group consisting of an alkylene group, a cycloalkylene group, an arylene group, a divalent group with at least one arylene and at least one alkylene group have been connected, —CO—, —CS—, —SO$_2$—, —CONH— or —SO$_2$NH—.

2. A color photosensitive material according to claim 1 wherein the compound is represented by the following formula:

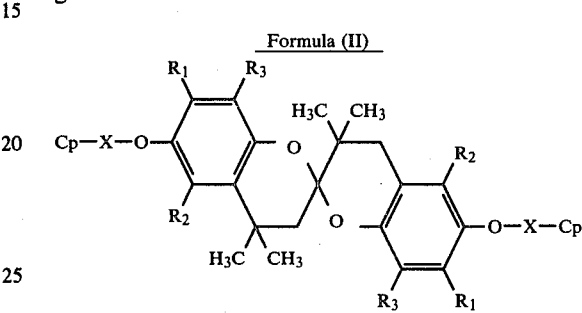

Formula (II)

wherein Cp, $R_1$, $R_2$, $R_3$ and X are as defined for formula (I).

3. A color photosensitive material according to claim 1 wherein $R_1$ represents hydrogen, or an alkyl group, and $R_2$ and $R_3$ individually represent hydrogen.

4. A color photosensitive material according to claim 3 wherein $R_1$ represents a methyl group.

5. A color photosensitive material according to claim 1 wherein Cp represents an acylacetonitrile yellow coupler residue, an acylacetoanilide yellow coupler residue, a 5-pyrazolone magenta coupler residue, a imidazolone magenta coupler residue, a pyrazolinobenzimidazole magenta coupler residue, a phenol cyan coupler residue, an α-naphthol cyan coupler residue or a pyrazoloquinazolone cyan coupler residue.

6. A color photosensitive material according to claim 5 wherein Cp represents a 5-pyrazolone magenta coupler residue.

7. A color photosensitive material according to claim 1 wherein X represents a simple bond or a straight or a branched alkylene group having 1 to 22 carbon atoms.

8. A color photosensitive material according to claim 2 wherein $C_p$ is represented by the following formula:

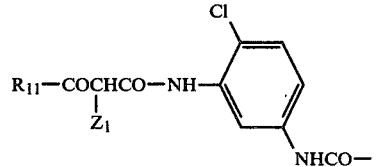

wherein $R_{11}$ represents an alkyl group, a terpenyl group, an aryl group or a heterocyclic ring, and $Z_1$ represents hydrogen or a split-off group selected from the group consisting of halogen, —OR', —OCOR', —SR', —OCONHR', —OSO$_2$NHR', —NHCOR', —NHSO$_2$R', wherein R' represents hydrogen, an alkyl group, or an aryl group; —SO$_3$H, —SCN, an azo group, or a 5- or 6-membered heterocyclic ring containing nitrogen, oxygen and/or sulfur.

9. A color photosensitive material according to claim 8 wherein $R_{11}$ represents an alkyl group or an aryl group.

10. A color photosensitive material according to claim 9 wherein $R_{11}$ represents a tert-alkyl group or a phenyl group.

11. A color photosensitive material according to claim 2 wherein $C_{p'}$ represents by the following formula:

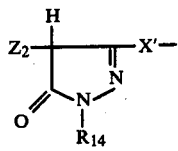

wherein $R_{14}$ represents an alkyl group, aryl group or a heterocyclic ring selected from the group consisting of pyridyl, quinolyl, furyl, thiazolyl, benzothiazolyl, oxazolyl, benzoxazolyl, imidazolyl, benzimidazolyl and naphthooxazolyl, X' represents

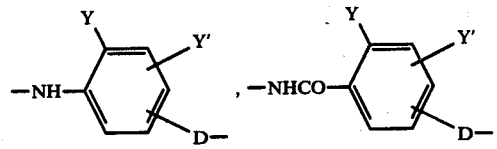

or —NHCO—, Y represents hydrogen, halogen, an alkyl group or an alkoxy group, Y' is Y, B represents hydrogen or an alkyl group, D represents —NHCO—, —CONH—, NHSO$_2$—, —SO$_2$NH— or

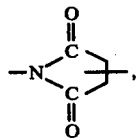

and $Z_2$ represents hydrogen or a split-off group selected from the group consisting of halogen, —OR', —OCOR', —SR', —OCONHR', —OSO$_2$NHR—, —NHCOR', —NHSO$_2$R' wherein R' represents hydrogen, an alkyl group, or an aryl group; —SO$_3$H, —SCN, an azo group, or a 5- or 6-membered heterocyclic ring containing nitrogen, oxygen and/or sulfur.

12. A color photosensitive material according to claim 11 wherein $R_{14}$ represents halogen-substituted phenyl, halogen-substituted alkylphenyl or halogen-substituted lower alkoxyphenyl.

13. A color photosensitive material according to claim 11 wherein X' represents

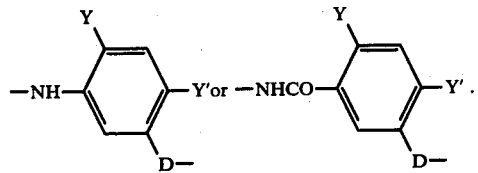

14. A color photosensitive material according to claim 2 wherein $C_p$ is represented by the following formula:

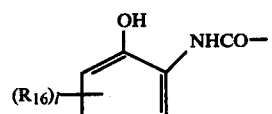
Formula (VI-a)

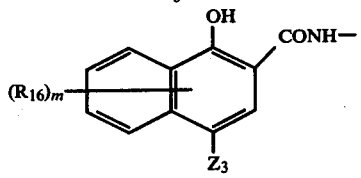
Formula (VII-a)

wherein $R_{16}$ represents hydrogen, halogen, an alkyl group, $Z_3$ represents hydrogen or a split-off group selected from the group consisting of halogen, —OR', —OCOR', —SR', —OCONHR', —OSO$_2$NHR', —NHCOR', —NHSO$_2$R' wherein R' represents hydrogen, an alkyl group, or an aryl group; —SO$_3$H, —SCH, an azo group, or a 5- or 6-membered heterocyclic ring containing nitrogen, oxygen, and/or sulfur, l represents 1–3 and m represents 1–5.

15. A color photosensitive material according to claim 14 wherein $R_{16}$ represents halogen or a methyl group.

* * * * *